(12) United States Patent
Tachibana

(10) Patent No.: US 11,944,262 B2
(45) Date of Patent: Apr. 2, 2024

(54) ENDOSCOPE PROCESSOR, INFORMATION PROCESSING DEVICE, AND ENDOSCOPE SYSTEM

(71) Applicant: HOYA CORPORATION, Tokyo (JP)

(72) Inventor: Toshio Tachibana, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 325 days.

(21) Appl. No.: 17/267,931

(22) PCT Filed: Mar. 27, 2019

(86) PCT No.: PCT/JP2019/013128
§ 371 (c)(1),
(2) Date: Feb. 11, 2021

(87) PCT Pub. No.: WO2020/194568
PCT Pub. Date: Oct. 1, 2020

(65) Prior Publication Data
US 2022/0000337 A1  Jan. 6, 2022

(51) Int. Cl.
*A61B 1/00* (2006.01)
*A61B 1/045* (2006.01)
*G06T 7/00* (2017.01)

(52) U.S. Cl.
CPC .. *A61B 1/000094* (2022.02); *A61B 1/000096* (2022.02); *A61B 1/045* (2013.01);
(Continued)

(58) Field of Classification Search
CPC ........ A61B 1/000094; A61B 1/000096; A61B 1/045; G06T 7/0012; G06T 2207/10068;
(Continued)

(56) References Cited

U.S. PATENT DOCUMENTS 8,682,142 B1 * 3/2014 Boskovitz ............ G11B 27/034
386/282
10,512,433 B2 * 12/2019 Ikemoto ............... A61B 5/1032
(Continued)

FOREIGN PATENT DOCUMENTS

CN    107256552 A    10/2017
CN    108615037 A    10/2018
(Continued)

OTHER PUBLICATIONS

International Search Report (ISR) dated Jul. 2, 2019 filed in PCT/JP2019/013128.
(Continued)

*Primary Examiner* — Brian P Yenke
(74) *Attorney, Agent, or Firm* — GREENBLUM & BERNSTEIN, P.L.C.

(57) ABSTRACT

To provide an endoscope processor (2) and the like that can output the aggregation results of lesions for each examination part. The endoscope processor (2) according to one aspect includes an image acquisition unit that acquires a captured image from a large-intestine endoscope (1), a part identification unit that identifies a part in a large intestine based on the captured image acquired by the image acquisition unit, a polyp extraction unit that extracts a polyp from the captured image, an aggregation unit that aggregates the number of polyps for each part identified by the part identification unit, and an output unit that outputs an endoscope image based on the captured image and an aggregation result aggregated by the aggregation unit.

10 Claims, 22 Drawing Sheets

(52) U.S. Cl.
CPC .. *G06T 7/0012* (2013.01); *G06T 2207/10068* (2013.01); *G06T 2207/30092* (2013.01)

(58) Field of Classification Search
CPC ........... G06T 2207/30092; G06T 2207/30032; G06V 2201/032
See application file for complete search history.

(56) References Cited

U.S. PATENT DOCUMENTS

| | | | |
|---|---|---|---|
| 11,191,423 B1* | 12/2021 | Zingaretti | G06T 19/00 |
| 11,308,614 B2* | 4/2022 | Sachdev | A61B 1/000094 |
| 11,423,318 B2* | 8/2022 | Zingaretti | G06F 18/24 |
| 11,449,988 B2 | 9/2022 | Kamon | |
| 11,468,563 B2 | 10/2022 | Fu et al. | |
| 2006/0106284 A1 | 5/2006 | Shouji et al. | |
| 2009/0074268 A1* | 3/2009 | Tanaka | G06T 7/0012 |
| | | | 382/128 |
| 2015/0181185 A1 | 6/2015 | Ikemoto et al. | |
| 2018/0098689 A1 | 4/2018 | On | |
| 2018/0225820 A1 | 8/2018 | Liang et al. | |
| 2019/0254569 A1 | 8/2019 | Asada et al. | |
| 2020/0008653 A1* | 1/2020 | Kamon | A61B 1/00055 |
| 2020/0146529 A1 | 5/2020 | Kono et al. | |
| 2020/0184645 A1 | 6/2020 | Kamon | |
| 2020/0258224 A1* | 8/2020 | Endo | A61B 1/0005 |
| 2020/0279368 A1* | 9/2020 | Tada | A61B 1/00016 |
| 2020/0279373 A1* | 9/2020 | Hussain | A61B 1/000096 |
| 2020/0337537 A1* | 10/2020 | Hirasawa | A61B 1/000096 |
| 2021/0012495 A1* | 1/2021 | Kamon | G16H 40/60 |
| 2021/0153808 A1* | 5/2021 | Tada | G16H 50/20 |
| 2021/0177248 A1* | 6/2021 | Usuda | G06V 10/764 |
| 2021/0235980 A1* | 8/2021 | Oosake | A61B 1/05 |
| 2021/0251470 A1* | 8/2021 | Kimura | A61B 1/0005 |
| 2021/0274999 A1* | 9/2021 | Kubota | G06T 7/70 |
| 2021/0280312 A1* | 9/2021 | Freedman | G06V 10/764 |
| 2021/0398274 A1* | 12/2021 | Nishide | H04N 25/60 |
| 2021/0407077 A1* | 12/2021 | Makino | A61B 1/00045 |
| 2022/0020496 A1* | 1/2022 | Saito | G06T 7/0012 |
| 2022/0160208 A1* | 5/2022 | Liao | A61B 5/202 |
| 2022/0198742 A1* | 6/2022 | Nishide | G06T 7/70 |
| 2022/0301159 A1* | 9/2022 | Byun | A61B 1/31 |
| 2022/0338717 A1* | 10/2022 | Kimura | G06T 7/0012 |
| 2022/0369920 A1* | 11/2022 | Freedman | G06T 7/0012 |
| 2022/0392068 A1 | 12/2022 | Fu et al. | |
| 2022/0414880 A1* | 12/2022 | Inoue | A61B 1/00009 |
| 2023/0154580 A1* | 5/2023 | Wang | G16H 50/20 |
| | | | 382/118 |
| 2023/0245311 A1* | 8/2023 | Takahashi | A61B 1/00055 |
| | | | 382/128 |
| 2023/0255467 A1* | 8/2023 | Ikenoyama | A61B 1/00045 |
| | | | 382/128 |
| 2023/0298589 A1* | 9/2023 | Madan | G16H 30/40 |
| | | | 704/9 |

FOREIGN PATENT DOCUMENTS

| | | |
|---|---|---|
| CN | 109447973 A | 3/2019 |
| JP | 2004-350734 A | 12/2004 |
| JP | 2009-110282 A | 5/2009 |
| JP | 2011-156203 A | 8/2011 |
| JP | 2014-18333 A | 2/2014 |
| WO | 2016/203548 A1 | 12/2016 |
| WO | 2018/051583 A1 | 3/2018 |
| WO | 2018/179991 A1 | 10/2018 |
| WO | 2019/016912 A1 | 1/2019 |
| WO | 2019/054265 A1 | 3/2019 |
| WO | WO 2019/054265 A1 | 3/2019 |

OTHER PUBLICATIONS

Chinese Office Action dated May 23, 2023, for Chinese family member Application No. 201980054212.9.

Japanese Office Action (JPOA) dated Oct. 12, 2021 for corresponding Japanese Patent Application No. 2020-199711.

* cited by examiner

FIG. 4

| PATIENT ID | GENDER | NAME |
|---|---|---|
| 0000001 | MALE | *** |

| AGGREGATION ID | PATIENT ID | AGGREGATION DATE | PART | | | | |
|---|---|---|---|---|---|---|---|
| | | | ASCENDING COLON | TRANSVERSE COLON | DESCENDING COLON | SIGMOID COLON | RECTUM |
| 000001 | 0000001 | 14:20:12 JANUARY 2, 2019 | 10 | 11 | 9 | 5 | 2 |

| AGGREGATION ID | POLYP ID | PART | MORPHOLOGY | NEOPLASTIC | BENIGNANCY/ MALIGNANCY | SIZE | CAPTURED TIME |
|---|---|---|---|---|---|---|---|
| 0000001 | 0000001_001 | ASCENDING COLON | Ip | TUMOR | BENIGN | 10 TO 20mm | 14:21:01 JANUARY 2, 2019 |
| | 0000001_002 | ASCENDING COLON | Isp | NON-TUMOR | -- | LESS THAN 10mm | 14:22:15 JANUARY 2, 2019 |

| AGGREGATION ID | PATIENT ID | AGGREGATION DATE | PART | | | | |
|---|---|---|---|---|---|---|---|
| | | | ASCENDING COLON | TRANSVERSE COLON | DESCENDING COLON | SIGMOID COLON | RECTUM |
| 000001 | 000001 | 14:23:12 JANUARY 2, 2019 | 3,6,9 | 0,10,11 | 4,4,8 | 0,3,7 | 0,5,1 |

| AGGREGATION ID | PATIENT ID | AGGREGATION DATE |
|---|---|---|
| 0000001 | 0000001 | 14:28:12 JANUARY 2, 2019 |

| PART | | | | | | | | | | | |
|---|---|---|---|---|---|---|---|---|---|---|---|
| ASCENDING COLON | | TRANSVERSE COLON | | DESCENDING COLON | | SIGMOID COLON | | RECTUM | |
| NUMBER OF TIMES OF EXTRACTION | NUMBER OF TIMES OF RESECTION | NUMBER OF TIMES OF EXTRACTION | NUMBER OF TIMES OF RESECTION | NUMBER OF TIMES OF EXTRACTION | NUMBER OF TIMES OF RESECTION | NUMBER OF TIMES OF EXTRACTION | NUMBER OF TIMES OF RESECTION | NUMBER OF TIMES OF EXTRACTION | NUMBER OF TIMES OF RESECTION |
| 2,6,9 | 2,1,0 | 0,10,11 | 0,3,2 | 4,4,8 | 0,1,1 | 0,3,7 | 0,0,2 | 8,5,1 | 4,1,0 |

FIG. 19

| AGGREGATION ID | POLYP ID | PART | MORPHOLOGY | NEOPLASTIC | BENIGNANCY/ MALIGNANCY | SIZE | CAPTURED TIME |
|---|---|---|---|---|---|---|---|
| 000001 | 000001_001 | ASCENDING COLON | Ip | TUMOR | BENIGN | 10 TO 20mm | 14:21:01 JANUARY 2, 2019 |
|  | 000001_002 | ASCENDING COLON | Isp | NON-TUMOR | - | LESS THAN 10mm | 14:22:15 JANUARY 2, 2019 |

273

| RESECTION SITUATION | PRE-RESECTION TREATMENT | POST-RESECTION TREATMENT | RESECTION TIME | NUMBER OF TIMES OF RESECTION |
|---|---|---|---|---|
| RESECTED | PHYSIOLOGICAL SALINE INJECTION | HEMOSTATIC | 14:22:12 JANUARY 2, 2019 | 1 |
| UNRESECTED | - | - | - | - |

ENDOSCOPE PROCESSOR, INFORMATION PROCESSING DEVICE, AND ENDOSCOPE SYSTEM

TECHNICAL FIELD

The present invention relates to an endoscope processor, an information processing device, an endoscope system, a program, and an information processing method.

BACKGROUND ART

In recent years, there is a technique for outputting a report at the same time as endoscopic examination. For example, Patent Literature 1 discloses a medical image recording device that shortens the time required for report creation and reduces the work load by sharing the data possessed by each medical device.

CITATION LIST

Patent Literature
  Patent Literature 1: JP 2004-350734 A

SUMMARY OF INVENTION

Technical Problem

However, in the invention according to Patent Literature 1, a report is created by automatically linking a lesion in a sketch diagram of an examination part and the endoscopic observation image of the lesion, but the aggregation result of the lesion (for example, a polyp, etc.) is not included in the report.

One aspect is to provide an endoscope processor and the like capable of outputting the aggregation result of the lesion for each examination part.

Solution to Problem

An endoscope processor according to one aspect includes an image acquisition unit that acquires a captured image from a large-intestine endoscope, a part identification unit that identifies a part in a large intestine based on the captured image acquired by the image acquisition unit, a polyp extraction unit that extracts a polyp from the captured image, an aggregation unit that aggregates the number of polyps for each part identified by the part identification unit, and an output unit that outputs an endoscope image based on the captured image and an aggregation result aggregated by the aggregation unit.

Advantageous Effects of Invention

In one aspect, it is possible to output the aggregation results of a lesion for each examination part.

BRIEF DESCRIPTION OF DRAWINGS

FIG. 4 is an explanatory diagram illustrating an example of a record layout of a patient DB.

FIG. 5 is an explanatory diagram illustrating an example of a record layout of an aggregation DB.

FIG. 6 is an explanatory diagram illustrating an example of a record layout of a polyp DB.

FIG. 15 is an explanatory diagram illustrating an example of a record layout of an aggregation DB of a first modification.

FIG. 18 is an explanatory diagram illustrating an example of a record layout of the aggregation DB of a second embodiment.

FIG. 19 is an explanatory diagram illustrating an example of a record layout of the polyp DB according to the second embodiment.

DESCRIPTION OF EMBODIMENTS

Hereinafter, the invention will be described in detail with reference to the drawings illustrating embodiments thereof.

First Embodiment

The first embodiment relates to a mode in which the number of polyps for each part in the large intestine is aggregated from the captured image acquired by the endoscope for the large intestine, and the aggregation result is output.

Figure 1:
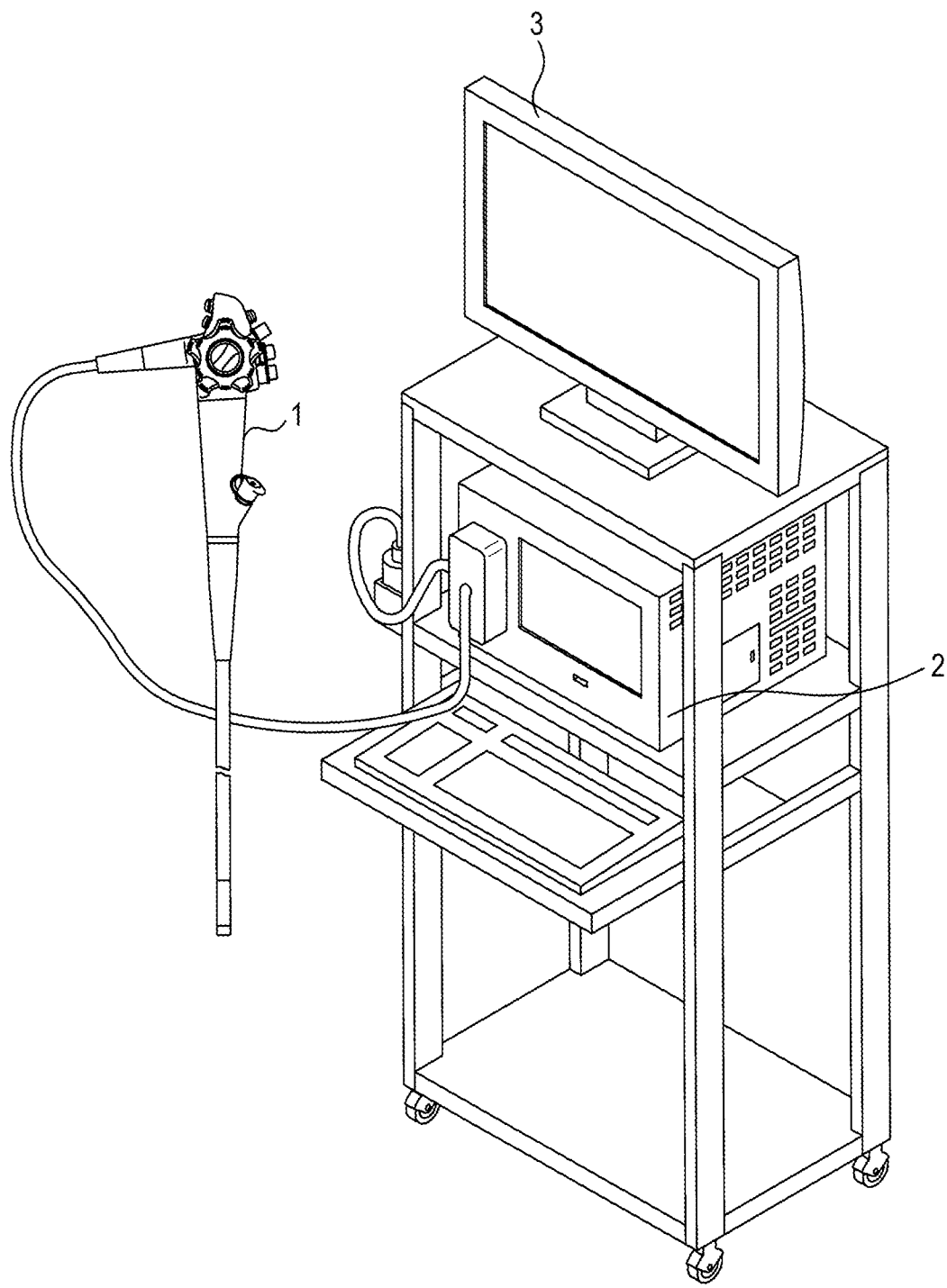
FIG. 1 is a schematic diagram illustrating a configuration example of an endoscope system for the large intestine that aggregates the number of polyps for each part in the large intestine.

FIG. 1 is a schematic diagram illustrating a configuration example of an endoscope system for the large intestine that aggregates the number of polyps for each part in the large intestine. The system illustrated in FIG. 1 includes a large-intestine endoscope 1 which is inserted into the lower gastrointestinal tract (large intestine) of a body to capture an image and outputs an electric signal of an observation target, an endoscope processor 2 which converts the electric signal output by the large-intestine endoscope 1 into a video signal, and a display device 3 which displays the captured image and the like of the observation target. Each device transmits and receives the electric signal, the video signal, and the like via a connector.

The large-intestine endoscope 1 is an instrument that inserts an insertion portion having an image sensor at the tip from the anus and performs diagnosis or treatment from the rectum to the end of the colon. The large-intestine endoscope 1 transfers the electric signal of the observation target captured by the image sensor at the tip to the processor 2. In the following, for the sake of brevity, the large-intestine endoscope 1 will be read as the endoscope 1.

The endoscope processor 2 is an information processing device that performs image processing on a captured image taken from the image sensor at the tip of the endoscope 1, generates an endoscope image, and outputs it to the display device 3. In the following, for the sake of brevity, the endoscope processor 2 will be read as the processor 2.

The display device 3 is a liquid crystal display, an organic EL (electroluminescence) display, or the like, and displays an endoscope image or the like output from the processor 2.

In this embodiment, the processor 2 identifies the part in the large intestine under observation from the captured image acquired from the endoscope 1. Further, the processor 2 extracts a polyp from the captured image. Then, the processor 2 aggregates the number of polyps extracted for each identified part in the large intestine, and outputs the endoscope image and the aggregation result to the display device 3.

Figure 2:
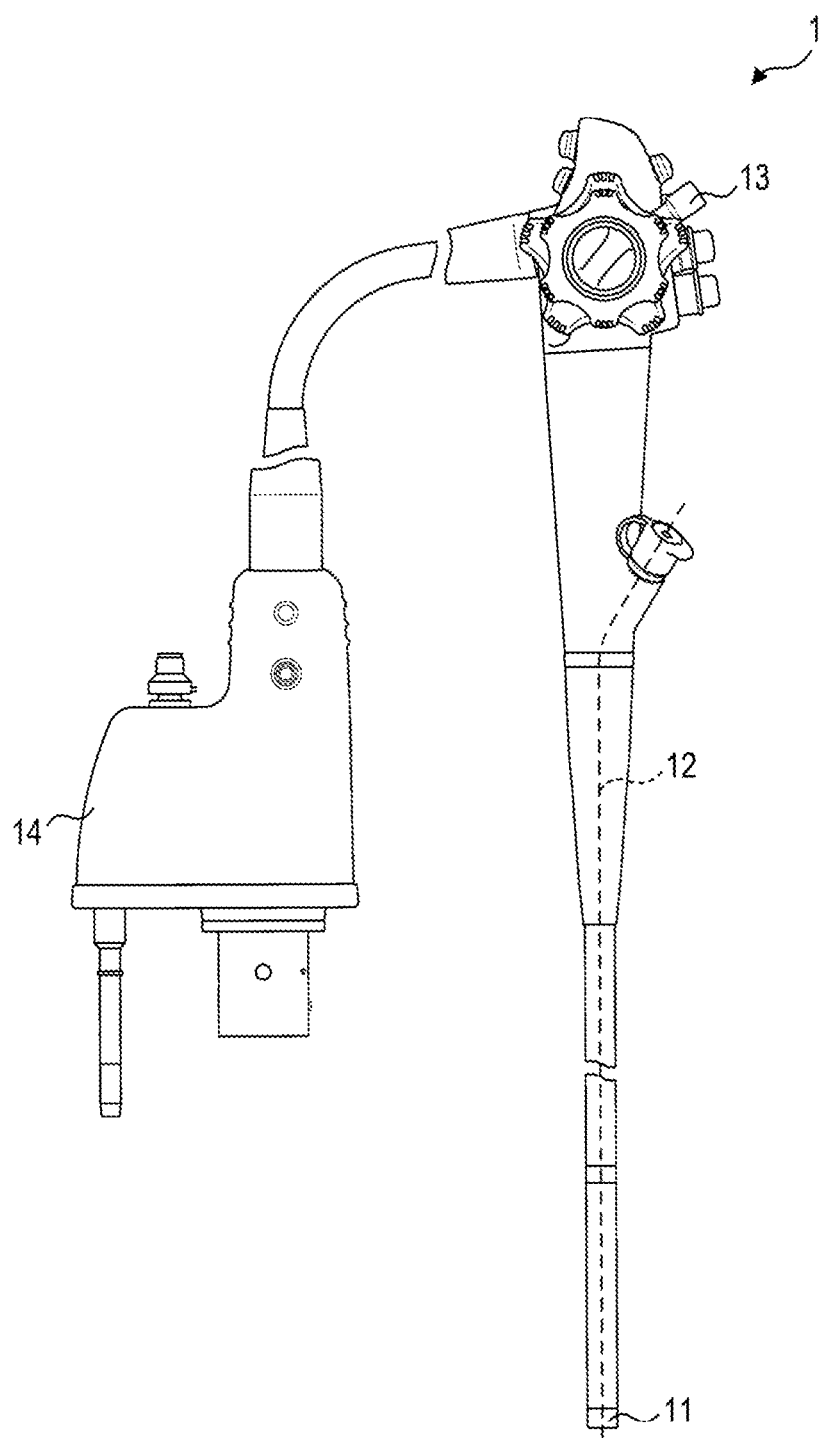
FIG. 2 is an exterior view of an endoscope.

FIG. 2 is an exterior view of the endoscope 1. The endoscope 1 includes an image sensor 11, a treatment tool insertion channel 12, an operation unit 13, and a connector 14. The image sensor 11 is installed at the tip portion of the endoscope 1, includes a CCD (Charge Coupled Device) image sensor, a CMD (Charge Modulation Device) image sensor, or a CMOS (Complementary Metal Oxide Semiconductor) image sensor, and photoelectrically converts the incident light. The electric signal generated by the photoelectric conversion is subjected to signal processing such as A/D conversion and noise removal by a signal processing circuit (not illustrated), and is output to the processor 2.

The treatment tool insertion channel 12 is a channel for passing the treatment tool. Examples of the treatment tools include grippers, biopsy needles, forceps, snares, clamps, scissors, scalpels, incision instruments, endoscope staplers, tissue loops, clip appliers, suture delivery instruments, energy-based tissue clotting instruments, or tissue cutting instruments. The operation unit 13 is provided with a release button, an angle knob for bending the tip of the endoscope, and the like, and receives operation instruction signals of peripheral devices such as air supply, water supply, and gas supply. The connector 14 is connected to the processor 2.

Figure 3:
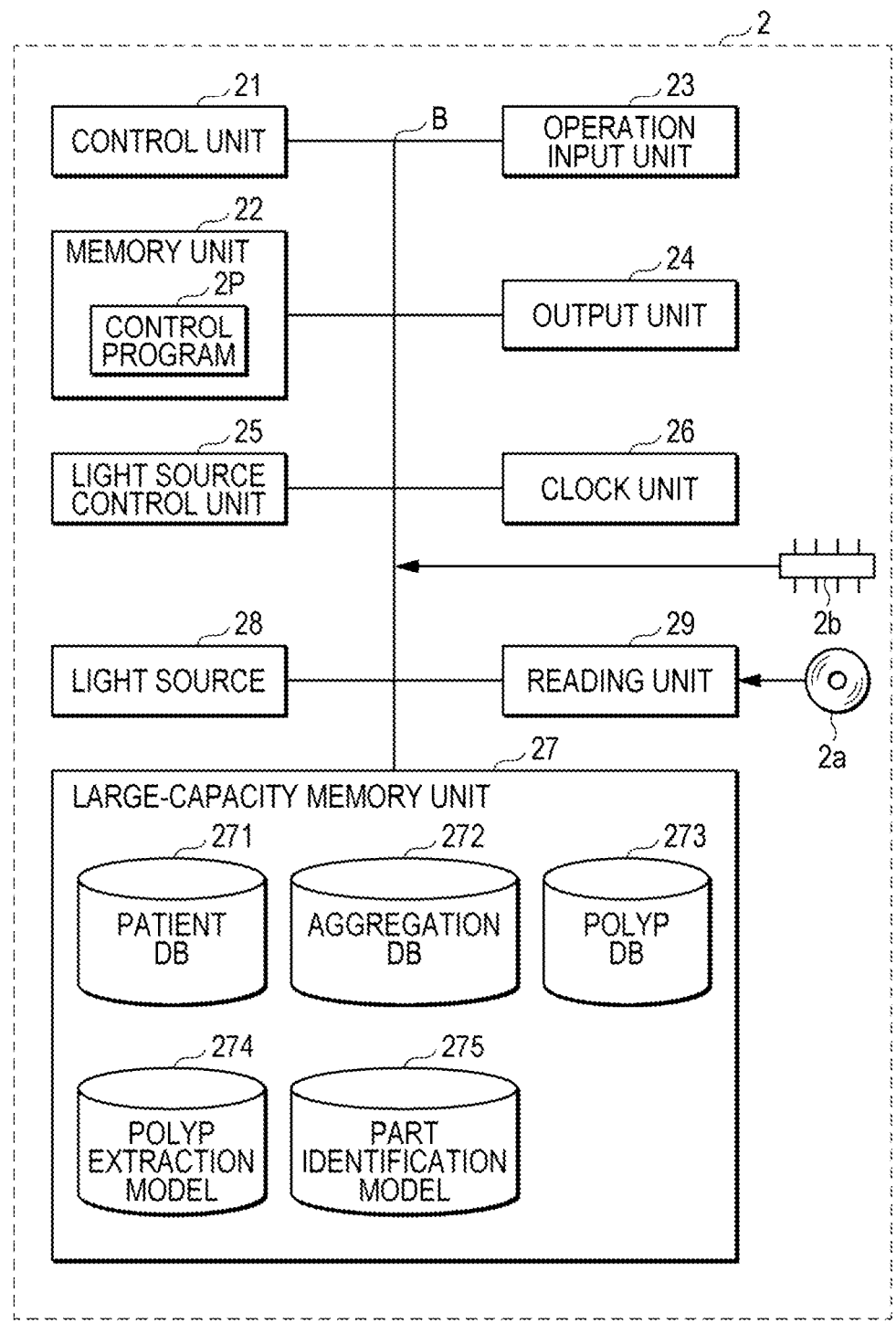
FIG. 3 is a block diagram illustrating a configuration example of a processor.

FIG. 3 is a block diagram illustrating a configuration example of the processor 2. The processor 2 includes a control unit 21, a memory unit 22, an operation input unit 23, an output unit 24, a light source control unit 25, a clock unit 26, a large-capacity memory unit 27, a light source 28, and a reading unit 29. Each configuration is connected by a bus B.

The control unit 21 includes arithmetic processing units such as a CPU (Central Processing Unit), an MPU (Micro-Processing Unit), and a GPU (Graphics Processing Unit), and reads and executes a control program 2P stored in the memory unit 22 to perform various information processing, control processing, and the like related to the processor 2. Although the control unit 21 is described as a single processor in FIG. 2, it may be a multiprocessor.

The memory unit 22 includes a memory element such as a RAM (Random Access Memory) and a ROM (Read Only Memory), and stores the control program 2P or data required for the control unit 21 to execute processing. In addition, the memory unit 22 temporarily stores data and the like necessary for the control unit 21 to execute arithmetic processing. The operation input unit 23 is configured by input devices such as a touch panel and various switches, and inputs an input signal generated in response to an external operation on these input devices to the control unit 21. Under the control of the control unit 21, the output unit 24 outputs an image signal for display and various types of information to the display device 3 to display the image and information.

The light source control unit 25 controls the amount of light emitted from the illumination light by turning on/off the LED and the like, adjusting the drive current and the drive voltage of the LED and the like. Further, the light source control unit 25 controls the wavelength band of the illumination light by changing the optical filter or the like. The light source control unit 25 adjusts the emission timing, emission period, light amount, and spectral spectrum of the illumination light by independently controlling the lighting and extinguishing of each LED and the amount of light emitted at the time of lighting. The clock unit 26 is a circuit that measures time, elapsed time, and the like, and gives a time measurement result to the control unit 21 in response to a request from the control unit 21.

The large-capacity memory unit 27 includes, for example, a recording medium such as an HDD (Hard disk drive) or an SSD (Solid State Drive). The large-capacity memory unit 27 includes a patient DB 271, an aggregation DB 272, a polyp DB 273, a polyp extraction model 274, and a part identification model 275. The patient DB 271 stores information about a patient. The aggregation DB 272 stores the aggregation result for the polyps extracted from the captured image. The polyp DB 273 stores information about the extracted polyps. The polyp extraction model 274 is an extractor that extracts polyps in the large intestine, and is a trained model generated by machine learning. The part identification model 275 is a part identifier that identifies a part in the large intestine, and is a trained model generated by machine learning.

In this embodiment, the memory unit 22 and the large-capacity memory unit 27 may be configured as an integrated memory device. Further, the large-capacity memory unit 27 may be configured by a plurality of memory devices. Furthermore, the large-capacity memory unit 27 may be an external memory device connected to the processor 2.

The light source 28 includes a light source that emits illumination light used for illuminating the observation target. The light source is, for example, a semiconductor light source such as a multi-color LED (Light Emitting Diode) having a different wavelength band, a combination of a laser diode and a phosphor, a xenon lamp, or the like. The light source 28 adjusts the brightness and the like according to the control from the light source control unit 25 of the processor 2. In this embodiment, the processor 2 is a light source integrated type, but the invention is not limited to this. For example, the processor 2 may be a light source separation type that is separated from the light source device.

The reading unit 29 reads a portable memory medium 2*a* including a CD (Compact Disc)-ROM or a DVD (Digital Versatile Disc)-ROM. The control unit 21 may read the control program 2P from the portable memory medium 2*a* via the reading unit 29 and store it in the large-capacity memory unit 27. Further, the control unit 21 may download the control program 2P from another computer via the network N or the like and store it in the large-capacity memory unit 27. Furthermore, the control unit 21 may read the control program 2P from a semiconductor memory 2*b*.

In this embodiment, the processor 2 is described as one information processing device, but a plurality of processors may be distributed for processing, or a virtual machine may be configured.

FIG. 4 is an explanatory diagram illustrating an example of the record layout of the patient DB 271. The patient DB 271 includes a patient ID field, a gender field, and a name field. The patient ID field stores a uniquely identified ID for a patient in order to identify each patient. The gender field stores the patient's gender. The name field stores the patient's name.

FIG. 5 is an explanatory diagram illustrating an example of the record layout of the aggregation DB 272. The aggregation DB 272 includes an aggregation ID field, a patient ID field, an aggregation date field, and a part field. The aggregation ID field stores the ID of the aggregation data that is uniquely identified in order to identify each aggregation data. The patient ID field stores the patient ID that identifies a patient. The aggregation date field stores date information in which the number of polyps is aggregated.

The part field includes an ascending colon field, a transverse colon field, a descending colon field, a sigmoid colon field, and a rectal field. The ascending colon field stores the number of polyps present in the ascending colon. The transverse colon field stores the number of polyps present in the transverse colon. The descending colon field stores the number of polyps present in the descending colon. The sigmoid colon field stores the number of polyps present in the sigmoid colon. The rectal field stores the number of polyps present in the rectum.

FIG. 6 is an explanatory diagram illustrating an example of the record layout of the polyp DB 273. The polyp DB 273 includes an aggregation ID field, a polyp ID field, a part field, a morphological field, a neoplastic field, a benignancy/malignancy field, a size field, and an imaging time field. The aggregation ID field stores the ID of the aggregation data that aggregates the number of polyps. The polyp ID field stores the ID of a uniquely identified ID for a polyp in order to identify each extracted polyp. The part field stores a part in the large intestine where the extracted polyp resides. The morphological field stores the morphological information of the polyp. The form of the polyp will be described later.

The neoplastic field stores diagnostic information on whether the polyp is neoplastic or non-neoplastic. The benignancy/malignancy field stores diagnostic information on whether the polyp is a benign tumor or a malignant tumor when the polyp is a neoplastic polyp. The size field stores the size of the polyp. The imaging time field stores date information when the polyp has been captured.

Figure 7:
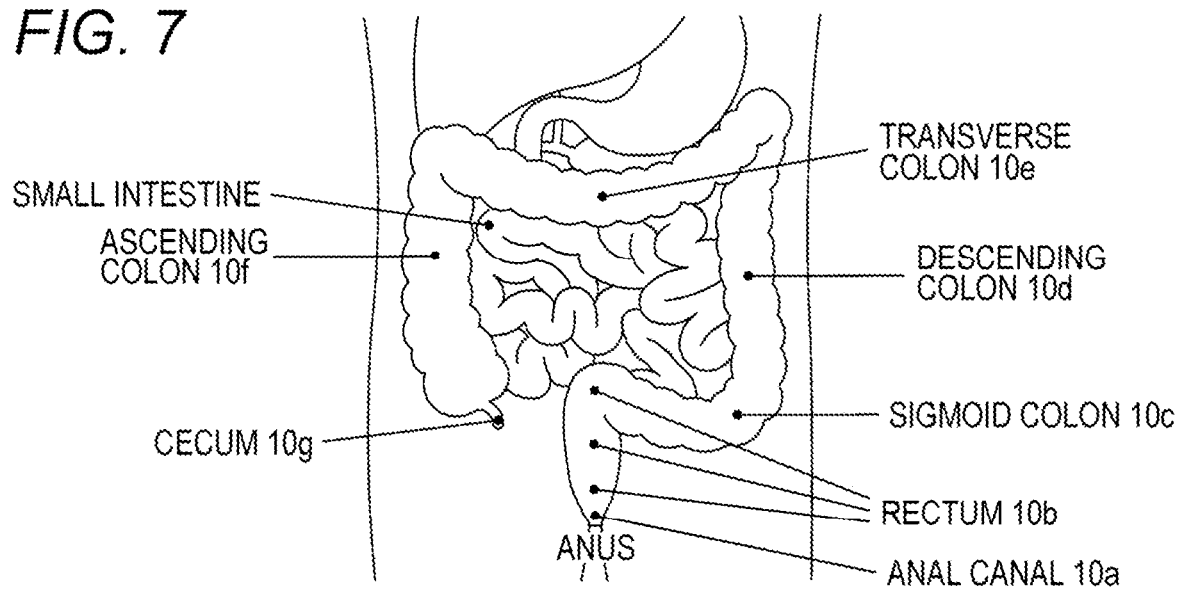
FIG. 7 is an explanatory diagram for explaining parts in the large intestine.

FIG. 7 is an explanatory diagram for explaining a part in the large intestine. The large intestine is an organ that starts from the lower right abdomen following the small intestine and goes around the abdomen in a large clockwise direction to connect to an anal canal 10*a*. The large intestine includes a cecum 10*g*, an ascending colon 10*f*, a transverse colon 10*e*, a descending colon 10*d*, a sigmoid colon 10*c*, and a rectum 10*b*. In addition, the rectum is not limited to the above-mentioned part, and for example, may be further divided into a rectal sigmoid part, an upper rectum, and a lower rectum.

Figure 8:
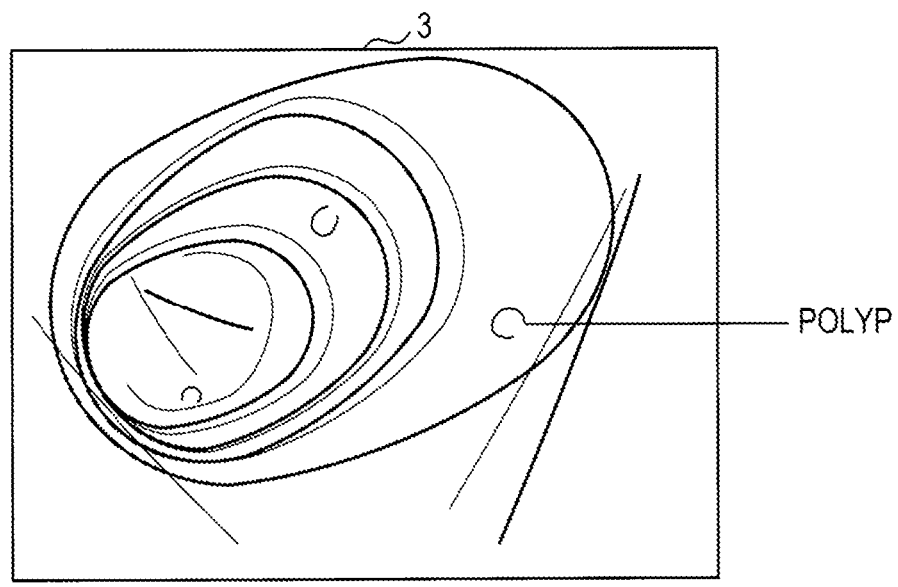
FIG. 8 is an explanatory diagram for explaining a polyp in the large intestine.

FIG. 8 is an explanatory diagram for explaining a polyp in the large intestine. As illustrated in the drawing, a polyp is a part of the mucous membrane of the large intestine that rises like a wart and protrudes into the space of the large intestine. Polyps can be classified according to the morphology, tissue type, or size of the polyp. For example, polyps are classified into a pedunculated type (Ip), a semipedunculated type (Isp), a sessile type (Is), and the like depending on the morphology of the polyp. Polyps are classified into neoplastic polyps and non-neoplastic polyps according to histological types. Neoplastic polyps include benign tumors and malignant tumors, and non-neoplastic polyps include hyperplastic polyps and inflammatory polyps. Polyps may be classified into, for example, "less than 10 mm", "10 to 20 mm" and "20 mm or more" according to their sizes.

Figure 9:
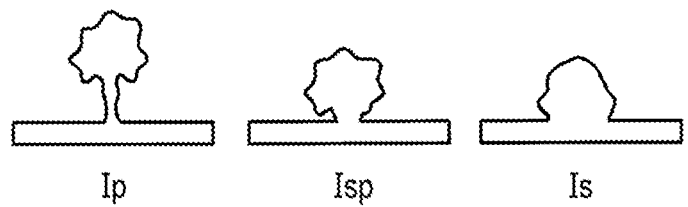
FIG. 9 is a schematic diagram illustrating the morphology of a polyp.

FIG. 9 is a schematic diagram illustrating the morphology of the polyp. The pedunculated type is a form in which the mucosal surface of the large intestine grows with a stem like a mushroom. The semipedunculated type is a form that the mucosal surface of the large intestine grows with a short stem that are not clear. The sessile type is a form in which the mucosal surface of the large intestine rises flat without a stern. Therefore, it is possible to extract the polyp from the captured image captured by the endoscope 1 based on the characteristics of each form of the polyp.

Next, a process of aggregating the number of polyps for each part in the large intestine will be described. The tip of the endoscope 1 is inserted into the anal canal 10*a*, passes through the rectum 10*b*, and inserted from the sigmoid colon 10*c* via the descending colon 10*d*, the transverse colon 10*e*, and the ascending colon 10*f* until it reaches the cecum 10*g*. The above-mentioned insertion route is a general insertion route for a large-intestine endoscope, and the cecum may not be inserted at the discretion of the doctor. The control unit 21 of the processor 2 determines whether the tip of the endoscope 1 has reached the cecum 10*g*. When the control unit 21 receives an instruction to complete the insertion of the endoscope at the doctor's discretion via the operation input unit 23, the control unit 21 may determine that the tip of the endoscope 1 has reached. When the tip of the endoscope 1 reaches the cecum, the insertion of the endoscope 1 is completed.

Figure 10:
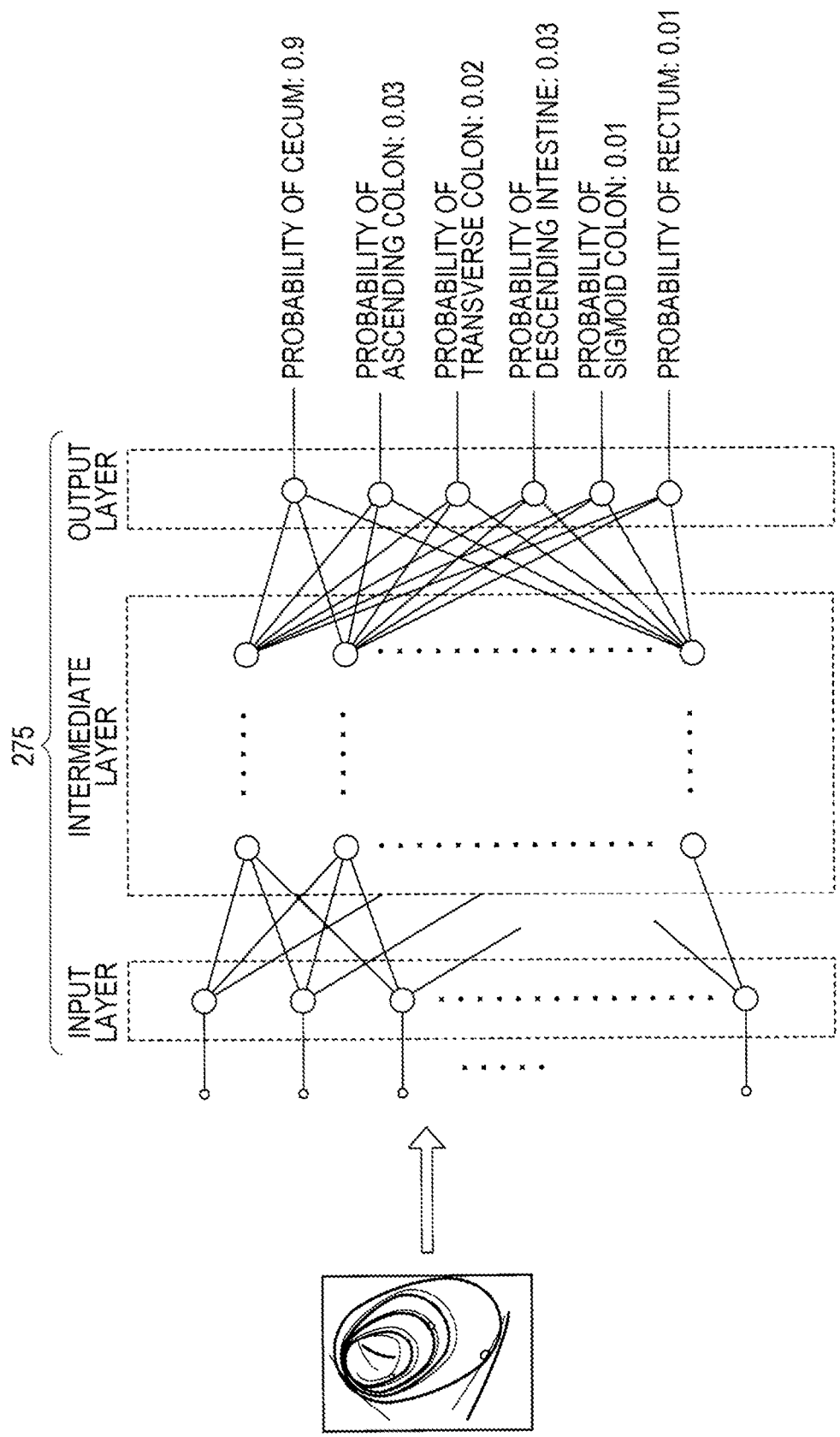
FIG. 10 is an explanatory diagram for explaining a part identification model.

FIG. 10 is an explanatory diagram for explaining the part identification model 275. The part identification model 275 is used as a program module that is part of artificial intelligence software. The part identification model 275 is an extractor for which a neural network has been constructed (generated) that receives a captured image captured in the large intestine acquired from the endoscope 1 and outputs a result of predicting a part in the large intestine. The neural network is, for example, a CNN (Convolutional Neural Network), and has an input layer that accepts an input of the captured image, an output layer that outputs the result of predicting a part in the large intestine, and an intermediate layer that has been trained by backpropagation.

The input layer has a plurality of neurons that receive an input of the pixel value of each pixel included in the captured image, and passes the input pixel value to the intermediate layer. The intermediate layer has a plurality of neurons for extracting an image feature amount of the captured image, and passes the extracted image feature amount to the output layer. For example, the case where the part identification model 275 is a CNN will be described as an example. The intermediate layer has a configuration in which a convolution layer that convolves the pixel value of each pixel input from the input layer and a pooling layer that maps the pixel values convoluted by the convolution layer are alternately connected, so that the feature amount of the image is finally extracted while compressing the pixel information of the captured image. After that, the intermediate layer predicts the probability that the captured image is each part in the large intestine by the fully-connected layer whose parameters are learned by backpropagation. The prediction result is output to the output layer having a plurality of neurons.

The captured image may be input to the input layer after the feature amount is extracted by passing through the convolution layer and the pooling layer which are alternately connected.

The process is not limited to the above-mentioned machine learning process for identifying a part. For example, the control unit 21 of the processor 2 may identify a part using a local feature amount extracting method such as A-KAZE (Accelerated KAZE), SIFT (Scale Invariant Feature Transform), or the like based on the change in color or folds in the large intestine from the captured image captured by the endoscope 1. Alternatively, the control unit 21 of the processor 2 may receive the identification result of the doctor identifying the part in the large intestine based on the medical expertise by the operation input unit 23.

The control unit 21 performs image processing on the captured image acquired from the image sensor 11 at the tip of the endoscope 1 to generate an endoscope image suitable for observation by a doctor. The generated endoscope image is displayed on the display device 3 in real time. The control unit 21 extracts a polyp from the captured image. In the following, the process of extracting polyps in the large intestine will be described using the polyp extraction model 274 constructed by deep learning.

Figure 11:
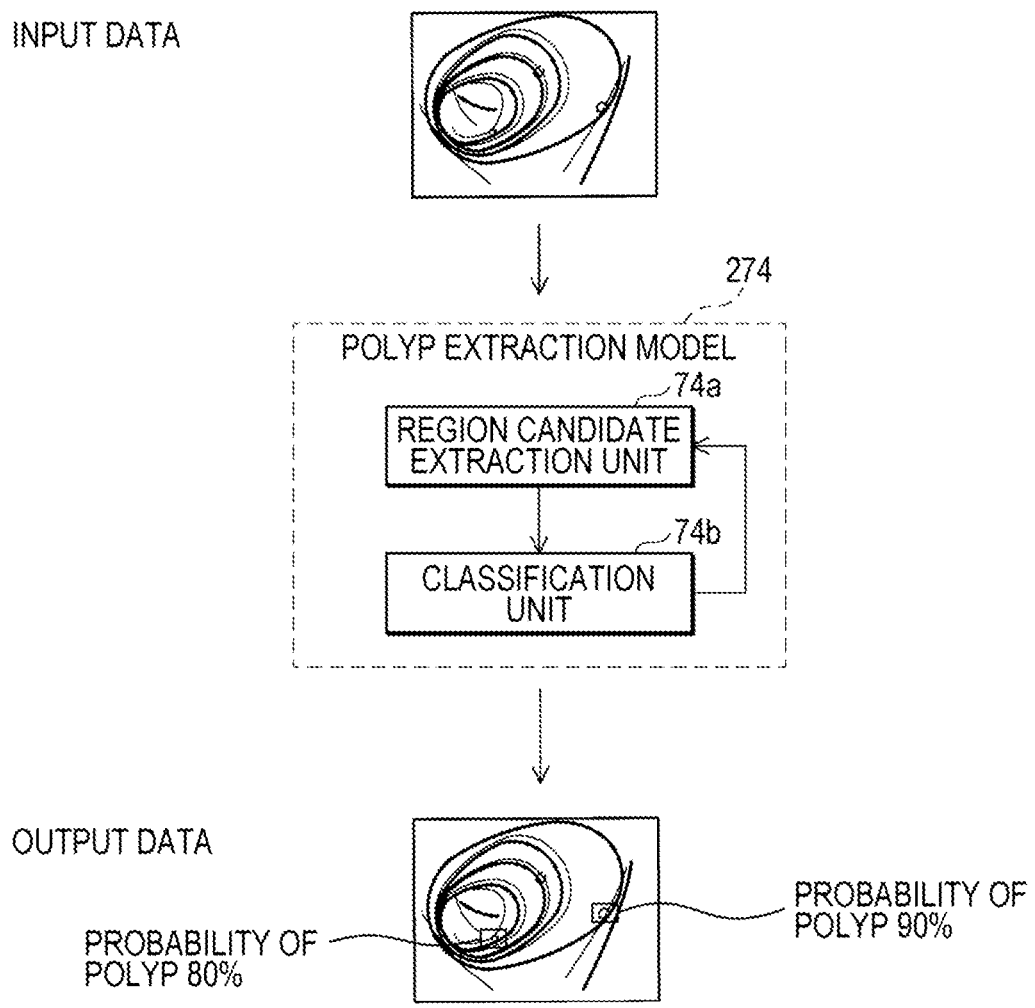
FIG. 11 is an explanatory diagram for explaining an outline of a polyp extraction process using a polyp extraction model.

FIG. 11 is an explanatory diagram for explaining an outline of the polyp extraction process using the polyp extraction model 274. The polyp extraction model 274 is used as a program module that is a part of artificial intelligence software. The polyp extraction model 274 is a learning model which outputs information indicating a region in which a polyp is presumed to appear and a probability that a polyp appears in the region in a case where the captured image in the large intestine acquired from the endoscope 1 is input.

The polyp extraction model 274 of this embodiment is estimated using RCNN (Regions with Convolutional Neural Network). The polyp extraction model 274 includes a region candidate extraction unit 74a and a classification unit 74b. The classification unit 74b includes a neural network (not illustrated). The neural network includes a convolution layer, a pooling layer, and a fully-connected layer.

The captured image is input to the polyp extraction model 274. The region candidate extraction unit 74a extracts region candidates of various sizes from the captured image. The classification unit 74b calculates the feature amount of the extracted region candidate, and classifies whether the object reflected in the region candidate is a polyp based on the calculated feature amount. The polyp extraction model 274 repeats the extraction and classification of region candidates.

The polyp extraction model 274 outputs the range of the region and the probability that the polyp appears for the region candidate classified as having the polyp appeared with a probability higher than a predetermined threshold. In the example illustrated in FIG. 11, a region in which a polyp appears with an 80% probability and a region in which a polyp appears with a 90% probability are detected.

The polyp extraction model 274 may be classify and output polyps with a probability of malignant polyps, a probability of benign polyps, a probability of pedunculated polyps, a probability of subpedunculated polyps, a probability of sessile type polyps, a probability less than 10 mm, a probability of 10 to 20 mm, or a probability of 20 mm or more.

Instead of RCNN, any object detection algorithm such as Fast RCNN, Faster RCNN or SSD (Single Shot Multibook Detector), YOLO (You Only Look Once) may be used.

The polyp extraction process is not limited to the extraction process method using a model in which the above-mentioned polyp characteristics are learned by deep learning or the like. For example, the control unit 21 of the processor 2 may accept the determination result, in which the doctor determines the polyp based on the specialized medical knowledge, by the operation input unit 23. Further, the control unit 21 of the processor 2 may recognize the captured image acquired from the endoscope 1 by using pattern matching or the like, and may recognize and extract the polyp from the captured image.

The control unit 21 of the processor 2 aggregates the number of polyps extracted for each identified part. The control unit 21 outputs the endoscope image based on the captured image and the aggregation result to the display device 3. The aggregation result includes a polyp ID, the number of polyps for each part, and the cumulative number of polyps.

That is, for the above-mentioned processing, the control unit 21 of the processor 2 identifies the part in the large intestine from the captured image captured by the endoscope 1. Further, the control unit 21 extracts a polyp from the captured image. The control unit 21 aggregates the number of polyps extracted for each identified part, and outputs the endoscope image based on the captured image captured from the endoscope 1 and the cumulative number of polyps for each part to the display device 3. In the process of pulling out the tip of the endoscope 1 from the cecum to the anus by this processing flow, the control unit 21 displays the aggregation result of polyps of each part through which the tip of the endoscope 1 has passed, and the endoscope image to the display device 3 at the same time.

Figure 12:
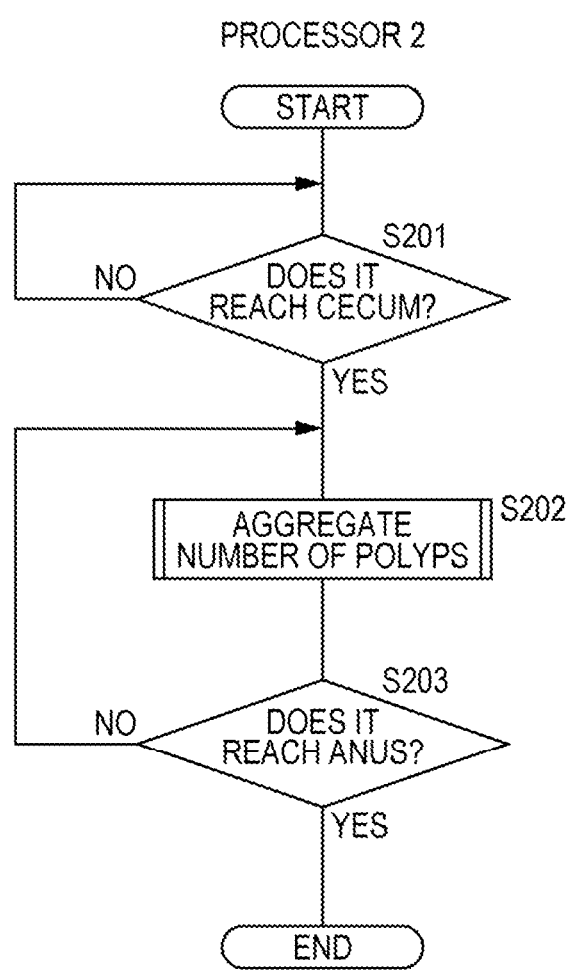
FIG. 12 is a flowchart illustrating an overall processing procedure when aggregating the number of polyps for each part in the large intestine.

FIG. 12 is a flowchart illustrating the entire processing procedure when aggregating the number of polyps for each part in the large intestine. The control unit 21 of the processor 2 determines whether the cecum has been reached based on the captured image captured from the endoscope 1 (Step S201). Specifically, the control unit 21 inputs the captured image into the part identification model 275 using the learned part identification model 275, and outputs the identification result for identifying the part. The control unit 21 identifies the part based on the identification result (for example, the probability value of the part) output from the output layer of the part identification model 275. For example, when the probability value of the cecum is equal to or higher than a predetermined threshold (for example, 0.85), the control unit 21 may determine that the tip of the endoscope 1 has reached the cecum.

When the control unit 21 determines that the cecum has not been reached (NO in Step S201), the control unit 21 returns to Step S201. When the control unit 21 determines that the cecum has reached (YES in Step S201), the control unit 21 executes a subroutine of a process for aggregating the number of polyps of each part when the tip of the endoscope 1 is pulled out in the direction opposite to the traveling direction (Step S202). The subroutine of the process for aggregating the number of polyps will be described later.

The control unit 21 inputs the captured image into the part identification model 275 using the learned part identification model 275, and outputs the identification result for identifying the part. The control unit 21 determines whether the anus has been reached based on the identification result output from the output layer of the part identification model 275 (Step S203). When the control unit 21 determines that the anus has not been reached (NO in Step S203), the control unit 21 returns to Step S202. When the control unit 21 determines that the anus has been reached (YES in Step S203), the control unit 21 ends the process.

Figure 13:
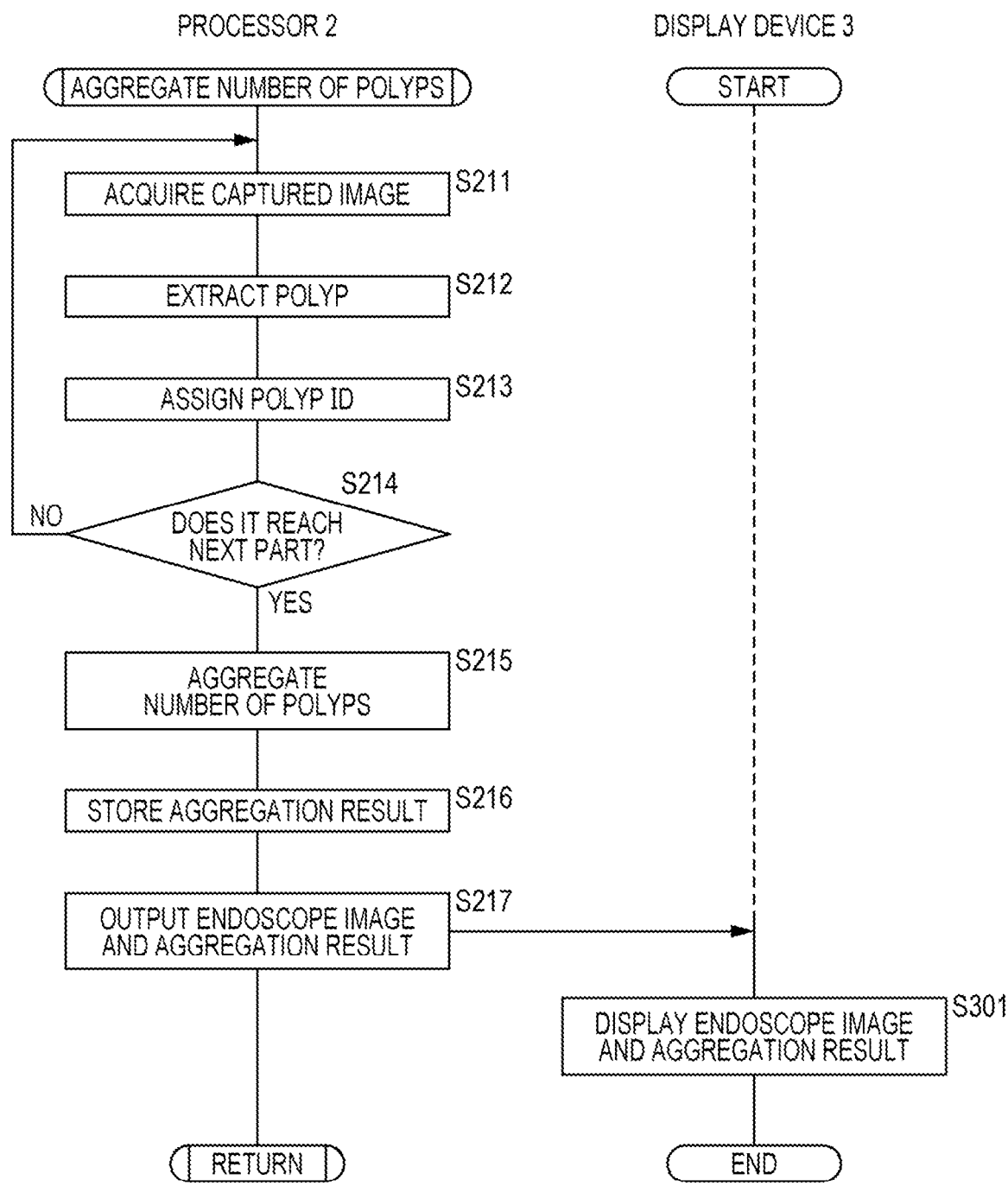
FIG. 13 is a flowchart illustrating a processing procedure of a subroutine of a process for aggregating the number of polyps for each part.

FIG. 13 is a flowchart illustrating a processing procedure of the subroutine of the process for aggregating the number of polyps for each part. The control unit 21 of the processor 2 acquires the captured image transferred from the endoscope 1 (Step S211). The control unit 21 inputs the captured image into the polyp extraction model 274 using the learned polyp extraction model 274, and acquires the extraction result of the polyp (Step S212). Regarding the polyp extraction process, for example, the above-mentioned polyp characteristics may be extracted using the polyp extraction model 274 that has been learned by deep learning or the like, or image recognition may be performed by pattern matching or the like to recognize and extract a polyp from the captured image.

The control unit 21 assigns a uniquely identified polyp ID to the extracted polyp (Step S213). The control unit 21 determines whether the next part (for example, the transverse colon) has been reached based on the acquired captured image (Step S214). When the control unit 21 determines that the next part has not been reached (NO in Step S214), the control unit 21 returns to Step S211. When the control unit 21 determines that the next part has been reached (YES in Step S214), the control unit 21 aggregates the number of polyps extracted for each part (Step S215).

The control unit 21 stores the aggregation result of polyps in the aggregation DB 272 and the polyp DB 273 of the large-capacity memory unit 27 (Step S216). Specifically, if the aggregation ID for this aggregation does not exist, the control unit 21 assigns an aggregation ID. The control unit 21 associates with the assigned aggregation ID based on the aggregation result of polyps, and stores the patient ID, the aggregation date, and the number of polyps of each part as one record in the aggregation DB 272. In addition, the control unit 21 stores the aggregation ID, polyp ID, part, morphology, neoplastic type (tumor/non-tumor), benignancy/malignancy (benignancy, malignancy), size, and imaging time as one record in the polyp DB 273 for each polyp. The timing of storing the aggregation result is not limited to the time immediately after the aggregation processing of each part described above, for example, the aggregation result may be stored at a time when the tip of the endoscope 1 reaches the anal canal 10a and the endoscopic examination is completed.

The control unit 21 outputs the endoscope image based on the captured image and the aggregation result of polyps to the display device 3 (Step S217). The display device 3 displays the endoscope image output from the processor 2 and the aggregation result of polyps (Step S301). The control unit 21 ends the subroutine of the process for aggregating the number of polyps and returns.

Figure 14A:
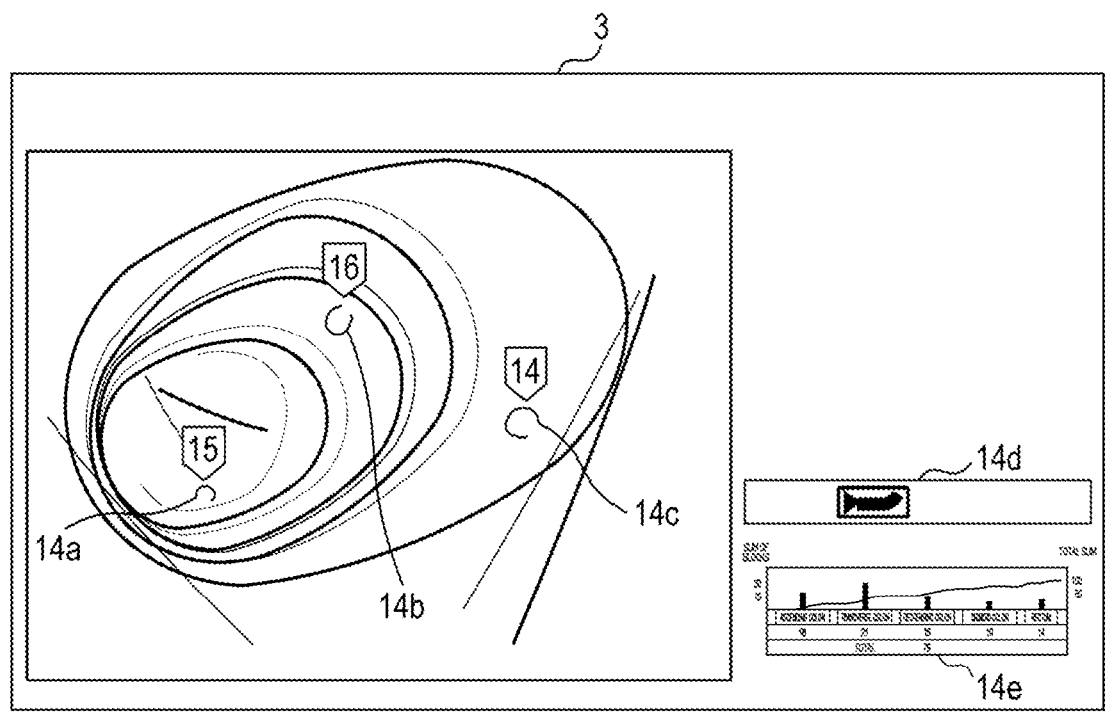
FIG. 14A is a schematic diagram illustrating the number and cumulative number of polyps aggregated for each part.

FIG. 14A is a schematic diagram illustrating the number and cumulative number of polyps aggregated for each part. The control unit 21 of the processor 2 identifies a part in the large intestine from the captured image acquired from the endoscope 1. The control unit 21 extracts a polyp from the captured image and assigns a polyp ID to the extracted polyp. The control unit 21 aggregates the number of polyps for each identified part, and outputs the endoscope image based on the captured image and the aggregation result to the display device 3.

As illustrated in the drawing, 14a, 14b and 14c represent the extracted polyps, and a tag indicating the polyp ID is displayed above each polyp. The polyp ID is provided to easily identify each polyp and does not have to be displayed in the endoscope image. 14d represents a current location indicator that indicates part information (position information) in the large intestine that the tip of the endoscope 1 has reached. The control unit 21 identifies a part where a polyp is present from the captured image, and outputs current location information indicating the distance relationship between the part and the entire passage route of the large intestine to the display device 3 based on the identified part. The display format of the current location indicator is not limited to the above-mentioned display format, and may be, for example, a display format of characters explaining the current location.

Figure 14B:
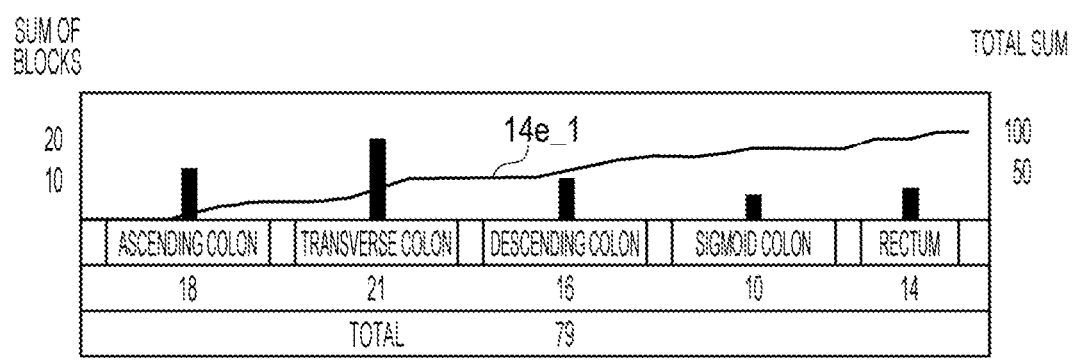
FIG. 14B is a graph illustrating the relationship between each part and the number of polyps in each part.

14e is a graph illustrating the relationship between each part and the number of polyps of each part. FIG. 14B is a graph illustrating the relationship between each part and the number of polyps in each part. FIG. 14B is an enlarged view of 14e. As illustrated in the drawing, the aggregation result of each part is displayed in a column graph based on the aggregated number of polyps for each of the ascending colon, the transverse colon, the descending colon, the sigmoid colon, and the rectum. The aggregation result includes the number of polyps of each part, the cumulative number of polyps, and the total number of polyps. The horizontal axis represents parts, and the vertical axis represents the number of polyps in each part. In addition, the number of polyps at each part and the total number of polyps are displayed at the bottom of the graph. 14e_1 is a polygonal line illustrating the relationship between each part in the large intestine and the cumulative number of polyps present in each part. The display format of the aggregation result is not limited to the column graph described above. For example, the aggregation result may be displayed as a line graph or a pie graph.

<First Modification>

The process of aggregating the number of polyps will be described for each division part in which the part where the polyp exists is further subdivided. The control unit 21 of the processor 2 determines the division part where a polyp is present, based on the time required for the endoscope 1 to pass through the part where the polyp is present and the time when the extracted polyp is captured, and aggregates the number of polyps extracted for each division part. The control unit 21 outputs the endoscope image and the aggregation result to the display device 3.

FIG. 15 is an explanatory diagram illustrating an example of the record layout of the aggregation DB 272 of the first modification. The contents overlapping with FIG. 5 are designated by the same reference numerals and the description thereof will be omitted. In FIG. 15, the part is further subdivided. For example, the ascending colon field stores the number of polyps per a division part. Based on the time required for the endoscope 1 to pass through the ascending colon where the polyp is present and the time when the polyp is captured, for example, the ascending colon is further divided into three parts along the direction in which the endoscope 1 is taken out. The number of polyps per a division part (for example, "3, 6, 9") may be stored in the ascending colon field. The transverse colon, descending colon, sigmoid colon, and rectal field are the same as the ascending colon field in terms of the method in which information is stored in the ascending colon field, and thus the description thereof will be omitted.

In the following, an example of dividing the ascending colon into division parts will be described, but since the division processing of other parts is the same, the description thereof will be omitted. The control unit 21 of the processor 2 uses the clock unit 26 to start timing from the time when the tip of the endoscope 1 is inserted into the cecum (starting part) and stops timing when the transverse colon (next part) is reached. The control unit 21 acquires the time when the tip of the endoscope 1 has passed, based on the start time and the end time measured by the clock unit 26. The acquired passing time is the time required for the tip of endoscope 1 to pass through the ascending colon. The control unit 21 allocates a division part for the ascending colon according to the passing time of the ascending colon. For example, if the time required for the endoscope 1 to pass through the ascending colon is 9 seconds, the control unit 21 of the processor 2 may further subdivide the ascending colon into three stages, including "0 to 3 seconds", "4 to 6 seconds", and "7 to 9" seconds depending on the passing time. Then, the control unit 21 identifies the position (division part) where each polyp exists based on the imaging time of each polyp extracted from the ascending colon, and aggregates the number of polyps for each assigned division part.

Figure 16:
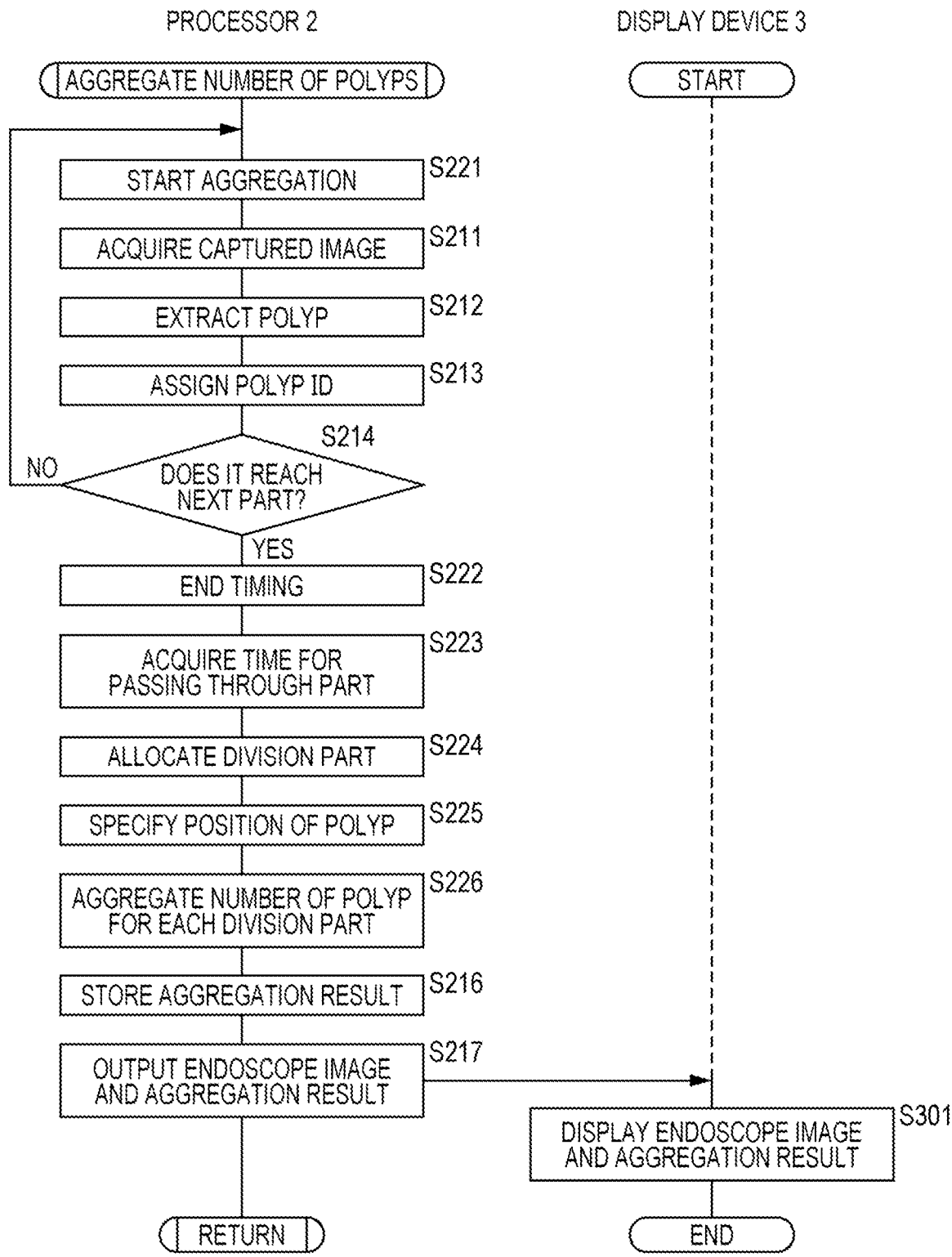
FIG. 16 is a flowchart illustrating a processing procedure of a subroutine of a process for aggregating the number of polyps for each division part.

FIG. 16 is a flowchart illustrating a processing procedure of a subroutine of processing for aggregating the number of polyps for each division part. The contents overlapping with FIG. 13 are designated by the same reference numerals and the description thereof will be omitted.

The control unit 21 of the processor 2 starts timing via the clock unit 26 (Step S221). Then, the control unit 21 executes Steps S211 to 213, inputs the captured image to the polyp extraction model 274 using the learned polyp extraction model 274, and outputs the extraction result for extracting the polyp. The extraction result of the polyp includes the capturing time of the extracted polyp. When the control unit 21 determines in Step S214 that the tip of the endoscope 1 has reached the next part, the control unit 21 ends the timing (Step S222).

The control unit 21 acquires the time required for the tip of the endoscope 1 to pass through the part based on the start time and the end time measured by the clock unit 26 (Step S223). The control unit 21 allocates a division part for the acquired part according to the time required for passing through the acquired part (Step S224). The control unit 21 identifies the position (division part) where each polyp exists based on the imaging time of each polyp extracted (Step S225), and aggregates the number of polyps for each assigned division part (Step S226).

Figure 17:
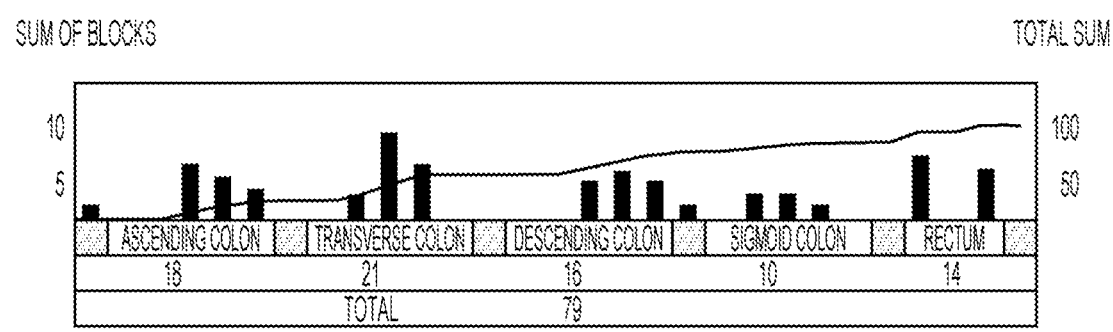
FIG. 17 is a graph illustrating the relationship between each division part and the number of polyps in each division part.

FIG. 17 is a graph illustrating the relationship between each division part and the number of polyps in each division part. FIG. 17 illustrates the number of polyps per division part instead of FIG. 14B. The description of the contents overlapping with FIG. 14B will be omitted. As illustrated in the drawing, the aggregation result of each division part is displayed in a column graph based on the aggregated number of polyps for each division part of the ascending colon, the transverse colon, the descending colon, the sigmoid colon, and the rectum. The aggregation result includes the number of polyps for each division part, the number of polyps of each part, the cumulative number of polyps, and the total number of polyps. The horizontal axis represents parts, and the vertical axis represents the number of polyps of each division part in each part. The display format of the aggregation result is not limited to the column graph described above. For example, the aggregation result may be displayed as a line graph or a pie graph.

According to this embodiment, since the polyps extracted from the captured image captured by the large-intestine endoscope are automatically aggregated for each part in the large intestine, the part where the polyp exists and the number of polyps in each part are visually displayed. This allows a doctor to clearly grasp the situation in the patient's large intestine.

According to this embodiment, it is possible to obtain highly accurate position information of a polyp by further subdividing each part in the large intestine.

Second Embodiment

The second embodiment relates to a mode in which, when polyps are resected, the number of resected polyps and the number of unresected polyps are aggregated for each part. The description of the contents overlapping with the first embodiment will be omitted.

Polyps in the large intestine are diseases in which wart-like ridges are formed on the mucous membrane of the large intestine, and most of them are benign diseases that do not harm the body immediately, but if they grow gradually, they may cause bleeding. It is known that some polyps in the large intestine develop a large intestine cancer via benign adenomatous polyps.

If it is in the polyp stage, it can be resected using the endoscope 1. For example, if the polyp classified by the morphology of the polyp is a pedunculated type and the size is "20 mm or more", the doctor may resect the polyp using a treatment tool such as a snare through the treatment tool insertion channel 12 of the endoscope 1. Specifically, the doctor puts out a snare from the treatment tool insertion channel 12, squeezes the snare (ring) while passing a high-frequency current through the operation unit 13, and completely resects the polyp from the root.

The control unit 21 of the processor 2 acquires and stores the resection information regarding the resected polyp from the captured image obtained by resecting the polyp. The process of acquiring the resection information is not limited to the method described above, and for example, the resection information of the polyp may be acquired manually by a doctor. The resection information includes the resected polyp ID, the resection time, the treatment before and after the resection, the number of times of resection, and the like. The control unit 21 aggregates the number of resected polyps and the number of unresected polyps for each part, and outputs the aggregation result to the display device 3.

FIG. 18 is an explanatory diagram illustrating an example of the record layout of the aggregation DB 272 of the second embodiment. The contents overlapping with FIG. 5 are designated by the same reference numerals and the description thereof will be omitted. The ascending colon field includes an extraction field and a resection field. The extraction field stores the number of polyps extracted from the ascending colon. When the ascending colon is further subdivided into division parts, the number of polyps for each division part may be stored. The resection field stores the number of times of resection of the resected polyp. As with the extraction field, the number of times of resection of the polyp for each division part may be stored.

The transverse colon contains an extraction field and a resection field. The descending colon contains an extraction field and a resection field. The sigmoid colon contains an extraction field and a resection field. The rectum contains an extraction field and a resection field. Since the configuration of each column described above is the same as that of the ascending colon field, the description thereof will be omitted.

FIG. 19 is an explanatory diagram illustrating an example of the record layout of the polyp DB 273 of the second embodiment. The contents overlapping with FIG. 6 are designated by the same reference numerals and the description thereof will be omitted. The polyp DB 273 includes a resection situation field, a pre-resection treatment field, a post-resection treatment field, a resection time field, and a resection frequency field. The resection situation field stores the situation of whether the extracted polyp was resected. For example, "resected", "unresected", or the like may be stored in the resection situation field.

The pre-resection treatment field stores treatment information prior to resection of the polyp. For example, "physiological saline injection" or the like may be stored. When a polyp classified according to the morphology of the polyp is a sessile type, it is difficult to snare and resect the polyp because it has a morphology that rises flatly from the mucosal surface of the large intestine without having a stem. In this case, the polyp can be lifted up by injecting physiological saline under the mucous membrane of the large intestine, and the raised portion can be resected by passing an electric current through a snare.

The post-resection treatment field stores treatment information after resection of the polyp. For example, treatment information such as "hemostatic with a clip or hemostat forceps" and "squeezing of a hole with a clip" may be stored. The resection time field stores the time when the polyp has been resected. The resection frequency field stores the number of times the polyp has been resected. For example, if the endoscope 1 cannot completely cut a large polyp at one time, the polyp may be cut out in several times.

Figure 20:
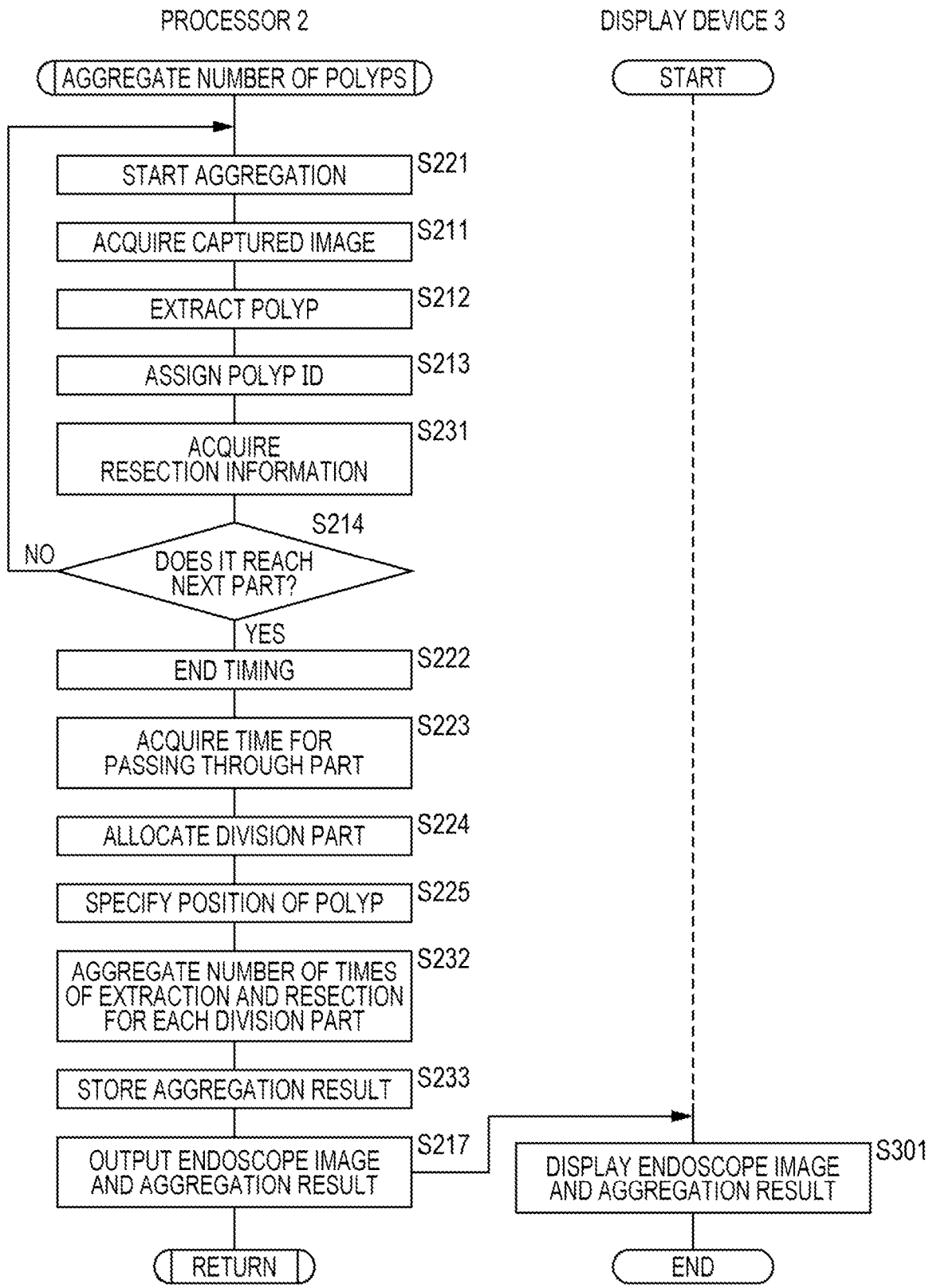
FIG. 20 is a flowchart illustrating a processing procedure of a subroutine of a process for aggregating the number of polyps extracted and the number of times of resection for each division part.

FIG. 20 is a flowchart illustrating a processing procedure of a subroutine of processing for aggregating the number of polyps extracted and the number of times of resection for each division part. The contents overlapping with FIG. 16 are designated by the same reference numerals and the description thereof will be omitted.

The control unit 21 of the processor 2 acquires resection information regarding the polyp resected by the doctor using the endoscope 1 (Step S231). The control unit 21 aggregates the number of polyps extracted and the number of times of resection for each division part (Step S232), and stores the aggregation result in the aggregation DB 272 and the polyp DB 273 of the large-capacity memory unit 27 (Step S233).

Specifically, if the aggregation ID for this aggregation does not exist, the control unit 21 assigns an aggregation ID. The control unit 21 associates with the assigned aggregation ID based on the aggregation result of the polyps, and stores the patient ID, the aggregation date, the number of polyps extracted at each part, and the number of times of resection as one record in the aggregation DB 272. In addition, the control unit 21 stores the aggregation ID, polyp ID, part, morphology, neoplastic type (tumor/non-tumor), benignancy/malignancy (benignancy, malignancy), size, imaging time, resection situation, pre-resection treatment, and post-resection treatment, resection time, and the number of times of resection for each polyp as one record in the polyp DB 273. The timing of storing the aggregation result is not limited to the time immediately after the aggregation processing of each part described above, for example, the aggregation result may be stored at a time when the tip of the endoscope 1 reaches the anal canal 10a and the endoscopic examination is completed.

Figure 21:
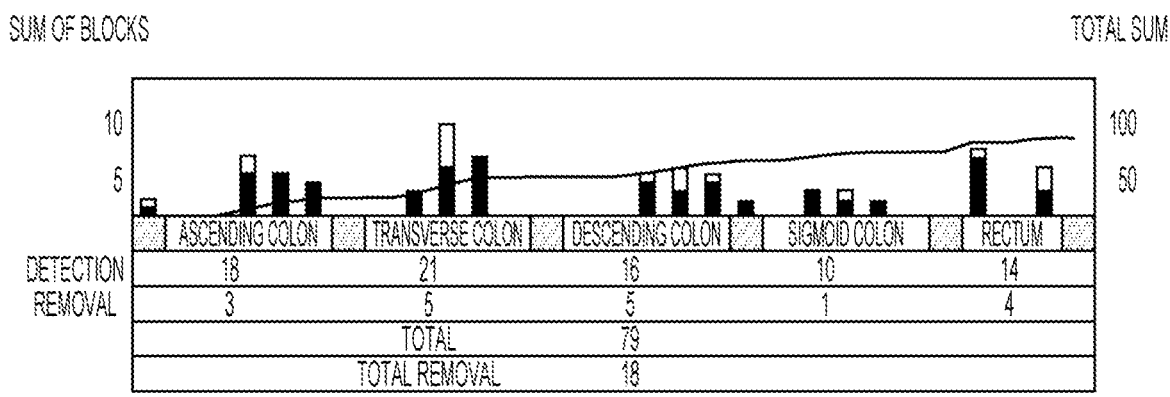
FIG. 21 is a graph illustrating the relationship between each part and the number of polyps extracted and the number of times of resection of each part.

FIG. 21 is a graph illustrating the relationship between each part and the number of polyps extracted and the number of times of resection of each part. FIG. 21 illustrates the number of polyps extracted and the number of times of resection for each part instead of FIG. 14B. The description of the contents overlapping with FIG. 14B will be omitted. As illustrated in the drawing, the aggregation result of each part is displayed in a column graph based on the number of aggregated polyps extracted and the number of times of resection for each of the ascending colon, the transverse colon, the descending colon, the sigmoid colon, and the rectum. The aggregation result includes the number of polyps extracted, the number of times of resection, and the cumulative number of polyps for each part. The horizontal axis indicates the part, the black vertical axis indicates the number of polyps extracted for each division part for each part, and the white vertical axis indicates the number of times of resection of polyps for each division part for each part. The display format of the aggregation result is not limited to the column graph described above. For example, the aggregation result may be displayed as a line graph or a pie graph.

According to this embodiment, it is possible to aggregate the number of resected polyps and the number of unresected polyps for the polyps extracted from the captured image captured by the large-intestine endoscope.

Third Embodiment

The third embodiment relates to a mode in which operation information performed during endoscopic examination is output. The description of the contents overlapping with the first and second embodiments will be omitted. The operations performed during endoscopic examination include normal observation, magnified observation, and observation using light. For example, an observation condition 1 may indicate the presence or absence of enlargement, and an observation condition 2 may indicate the type of illumination light.

The normal observation of the observation condition 1 is an observation operation with a normal zoom magnification. The magnified observation of the observation condition 1 is an observation operation using means such as magnifying the zoom magnification. Further, the magnified observation may be used in combination with, for example, spraying a pigment. Specifically, a doctor sprays a pigment such as indigo carmine at a high concentration of about 0.2% on the surface of the polyp through the treatment tool insertion channel 12 of the endoscope 1. The doctor may observe, for example, by magnifying the zoom magnification by 100 times.

Figure 22:
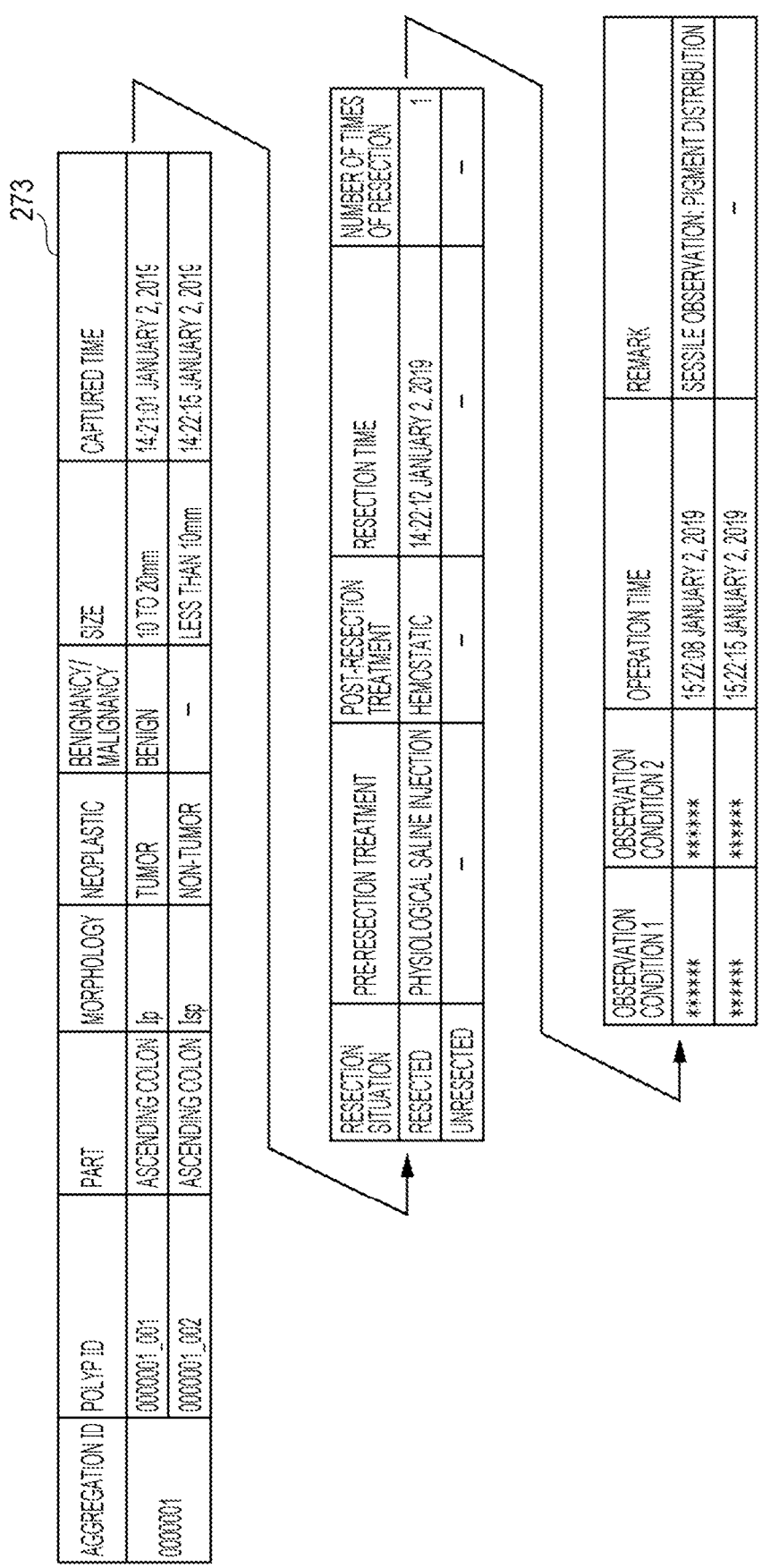
FIG. 22 is an explanatory diagram illustrating an example of a record layout of the polyp DB of a third embodiment.

FIG. 22 is an explanatory diagram illustrating an example of the record layout of the polyp DB 273 of the third embodiment. The contents overlapping with FIG. 19 are designated by the same reference numerals and the description thereof will be omitted. The polyp DB 273 includes an observation condition 1 field, an observation condition 2 field, an operation time field, and a remarks field. The observation condition 1 field stores an observation condition such as normal observation or magnified observation. The observation condition 2 field stores an observation condition such as observation using light. The operation time field stores the last operation time corresponding to either the observation condition 1 or the observation condition 2. The remarks field stores the content of the supplementary explanation for the polyp.

Figure 23:
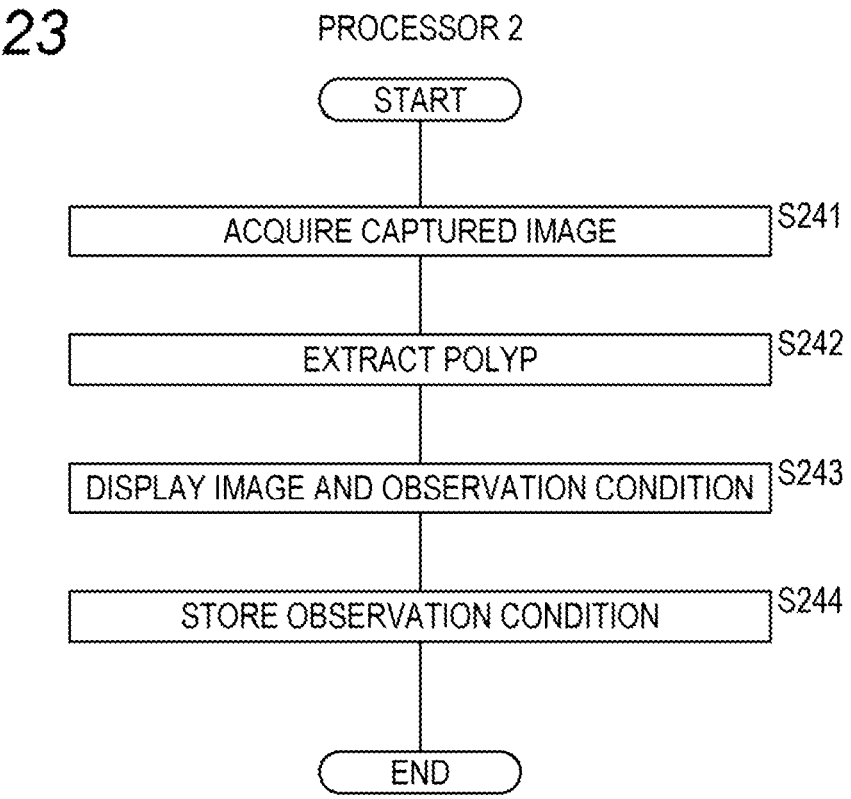
FIG. 23 is a flowchart illustrating a processing procedure for displaying an observation condition for a polyp.

FIG. 23 is a flowchart illustrating a processing procedure when displaying the observation condition for the polyp. The control unit 21 of the processor 2 acquires the captured image transferred from the endoscope 1 (Step S241). The control unit 21 extracts a polyp from the acquired captured image (Step S242). Since the polyp extraction process is the same as that in the first embodiment, the description thereof will be omitted.

The control unit 21 causes the display device 3 to display the endoscope image, the observation condition 1 including the zoom magnification, and the observation condition 2 including the white light observation or the special light observation (Step S243). The observation condition 1 and the observation condition 2 may be used separately or in combination. The control unit 21 associates the observation condition 1 and the observation condition 2 with the polyp ID, and stores them in the polyp DB 273 of the large-capacity memory unit 27 (Step S244). Specifically, the control unit 21 associates with the largest polyp ID in the captured image, and stores the observation condition 1, the observation condition 2, the operation time, and the remarks as one record in the polyp DB 273.

In addition, the observation conditions corresponding to the polyp operated during the endoscopic examination can be stored in the polyp DB 273 of the large-capacity memory unit 27. Specifically, the control unit 21 stores the aggregation ID, polyp ID, part, morphology, neoplastic type (tumor/non-tumor), benignancy/malignancy (benignancy, malignancy), size, imaging time, resection situation, pre-resection treatment, and post-resection treatment, resection time, the number of times of resection, the observation condition 1, the observation condition 2, the operation time, and the remarks for each polyp as one record in the polyp DB 273. Regarding the timing of the memory processing of the observation conditions, as in the first embodiment, the timing may be stored immediately after the aggregation processing of each part in the large intestine, or may be stored at a time when the tip of the endoscope 1 reaches the anal canal 10a, and the endoscopic examination ends.

Figure 24:
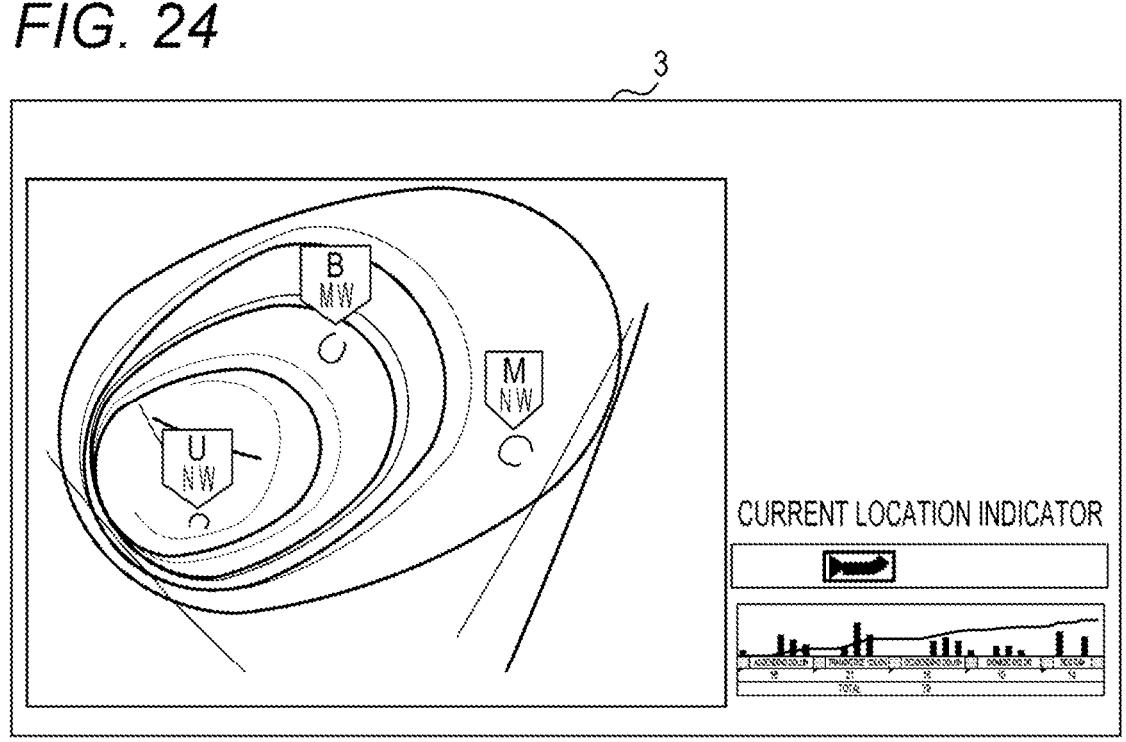
FIG. 24 is a schematic diagram for displaying operation information performed during endoscopic examination in a tab format.

FIG. 24 is a schematic diagram for displaying operation information performed during endoscopic examination in a tab format. The control unit 21 of the processor 2 has extracted three polyps from the captured image captured by the endoscope 1. The control unit 21 acquires benignancy/malignancy information for each extracted polyp. Regarding the benignancy/malignancy determination process, for example, the polyp extraction model 274 may be used to acquire a benignancy/malignancy probability value, and the benignancy/malignancy may be determined according to the acquired probability value. The control unit 21 acquires the observation condition 1 and the observation condition 2, and outputs the acquired benign/malignant type, the observation condition 1, and the observation condition 2 to the display device 3.

As illustrated in the drawing, the display device 3 displays the benign/malignant type, observation condition 1, and observation condition 2 output from the processor 2 in a tag format above the polyp. The tags attached to the polyp include a benign/malignant type, observation condition 1, and observation condition 2. For example, the benign type is indicated by B (Benign), the malignant type is indicated by M (Malignant), and an undetermined type is indicated by U (Undefined). The normal observation is indicated by N (Normal), and the magnified observation is indicated by M (Magnified). The white light observation is indicated by W (White), and the special light observation is indicated by S (Special).

The observation condition is not limited to the above-mentioned observation condition. For example, the tag of a polyp may display the benign/malignant determination state by blinking. The display device 3 displays the tag of the determined polyp as it is without blinking, and displays the tag of the undetermined polyp in blinking. In addition, the certainty may be displayed in a frame according to the probability value of the benign/malignant type. For example, the tag of a polyp with a high certainty of malignancy may be displayed in a thick frame. The tag of a polyp with a low certainty of malignancy may be displayed in a narrow frame. Furthermore, for example, if a benign or malignant polyp is large in size and resection is recommended, the display device 3 may display with a fast blinking.

According to this embodiment, by displaying a tag indicating observation condition and the like for the polyp extracted from the captured image, it is possible to assist the doctor's diagnosis and prevent the polyp from being overlooked or omission of resection.

Fourth Embodiment

The fourth embodiment relates to a mode in which the past aggregation result for the same patient and the current aggregation result are output at the same time. The description of the contents overlapping with the first to third embodiments will be omitted. The control unit 21 of the processor 2 can acquire the past aggregation result and the current aggregation result from the aggregation DB 272 of the large-capacity memory unit 27 based on the patient ID and the aggregation date. The control unit 21 outputs the acquired past aggregation result and the current aggregation result to the display device 3.

Figure 25:
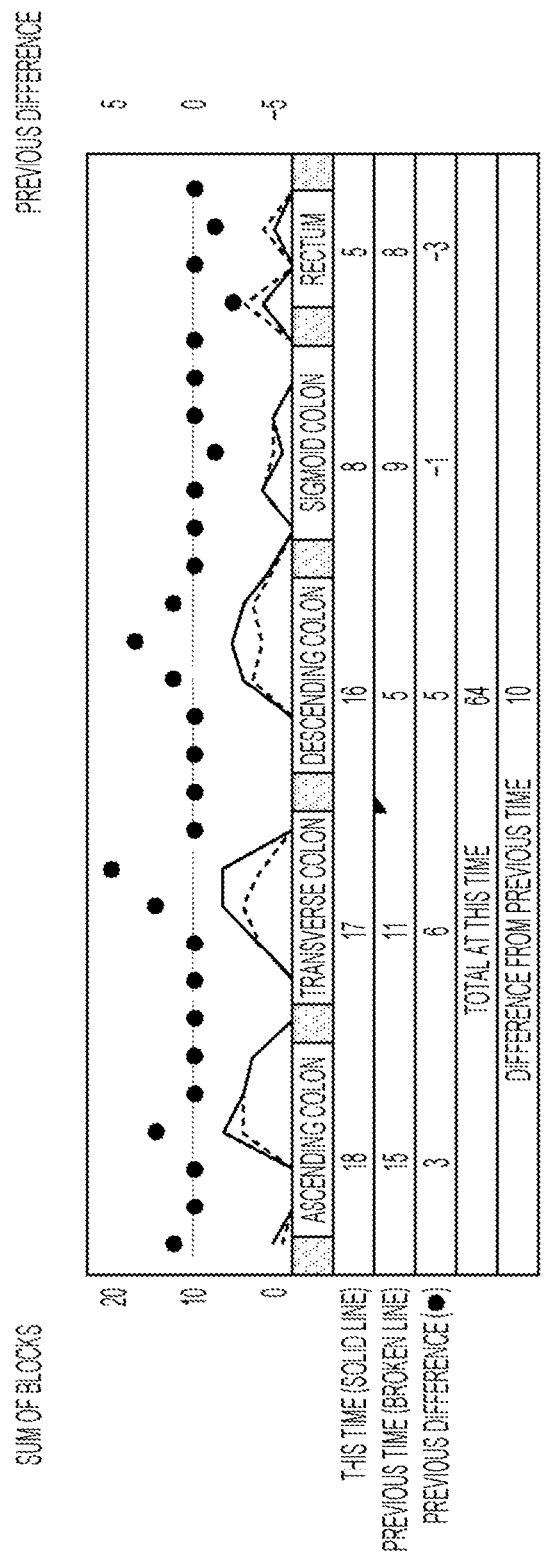
FIG. 25 is a graph illustrating the number of polyps extracted and the number of previous extractions at the same time for each part.

FIG. 25 is a graph illustrating the number of polyps extracted and the number of previous extractions at the same time for each part. The control unit 21 of the processor 2 aggregates the number of polyps for each part, and then acquires the previous aggregation result from the aggregation DB 272 of the large-capacity memory unit 27 based on the patient ID and the aggregation date. The control unit 21 outputs the current aggregation result and the acquired previous aggregation result to the display device 3 in a graph format. The display device 3 displays the current aggregation result and the previous aggregation result output from the processor 2.

As illustrated in the drawing, the distribution of the number of polyps for each part aggregated this time is shown by a solid polygonal line, and the distribution of the number of polyps for each part aggregated last time is shown by a broken polygonal line. The distribution of the difference between the number of polyps aggregated this time and the number of polyps aggregated last time is shown in points. In addition, the number of polyps for each part aggregated this time, the number of polyps for each part aggregated last time, the total number of polyps aggregated this time, and the difference between the total number of polyps aggregated this time and the total number of polyps aggregated last time are displayed in the lower side of the graph. The display format is not limited to the above-mentioned display format, and may be displayed, for example, in a column graph.

According to this embodiment, by simultaneously outputting the past aggregation result and the current aggregation result for each patient, it is possible to provide information such as the progress status of the polyp so far and the prediction of the progress of the polyp in the future.

Fifth Embodiment

Figure 26:
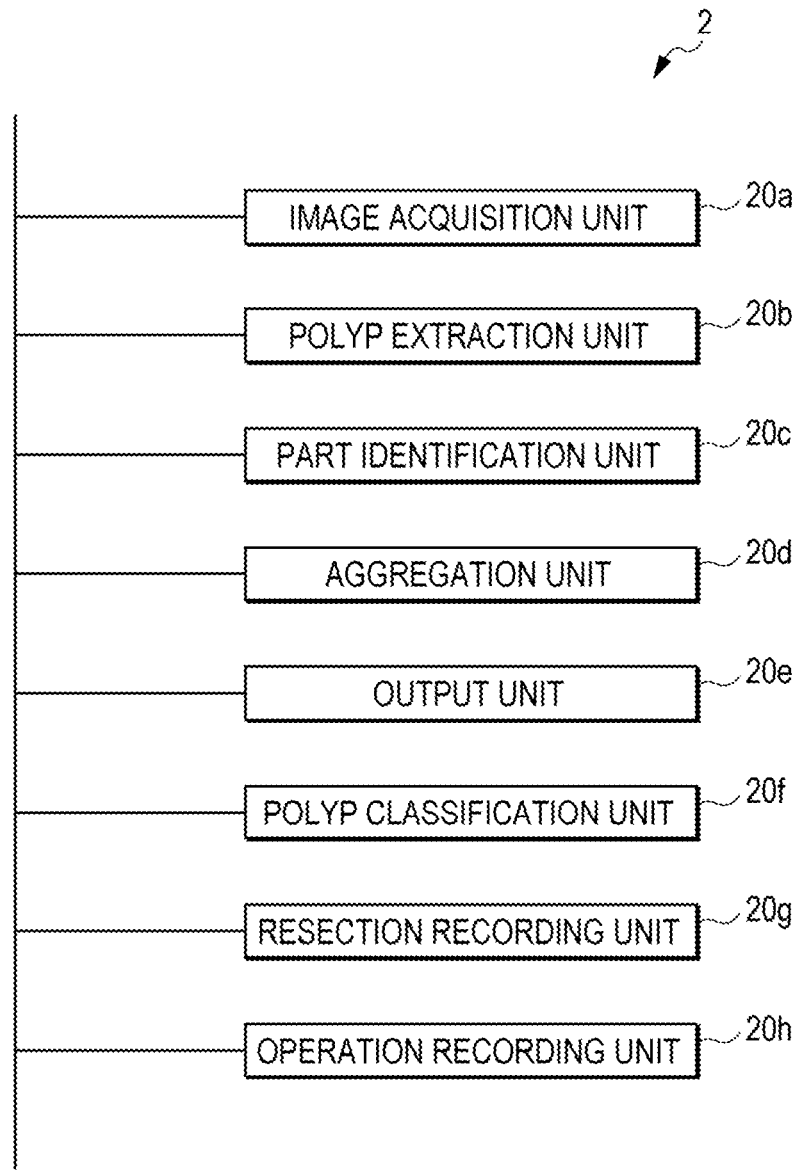
FIG. 26 is a functional block diagram illustrating the operation of the processor of the above-described embodiments.

FIG. 26 is a functional block diagram illustrating the operation of the processor 2 of the above-described embodiment. When the control unit 21 executes the control program 2P, the processor 2 operates as follows.

An image acquisition unit 20a acquires a captured image from the endoscope 1. A polyp extraction unit 20b extracts a polyp from the captured image acquired by the image acquisition unit 20a. A part identification unit 20c identifies the part in the large intestine where the polyp extracted by the polyp extraction unit 20b is present. An aggregation unit 20d aggregates the number of polyps extracted by the polyp extraction unit 20b for each part identified by the part identification unit 20c. An output unit 20e outputs an endoscope image based on the captured image acquired by the image acquisition unit 20a and the aggregation result aggregated by the aggregation unit 20d. A polyp classification unit 20f classifies the polyps extracted by the polyp extraction unit 20b. A resection recording unit 20g records whether the polyp has been resected. An operation recording unit 20h records the operation performed during the endoscopic examination and the operation time in association with each other.

The fifth embodiment is as described above, and the other portions are the same as those of the first to fourth embodiments. Therefore, the corresponding portions are designated by the same reference numerals and detailed description thereof will be omitted.

The embodiments disclosed herein are exemplary in all respects, and it should be considered that the embodiments are not restrictive. The scope of the invention is defined not by the above-described meaning but by claims, and intends to include all modifications within meaning and a scope equal to claims.

Reference Signs List 1 large-intestine endoscope (endoscope)
11 image sensor
12 treatment tool insertion channel
13 operation unit
14 connector
2 endoscope processor (processor)
21 control unit
22 memory unit
23 operation input unit
24 output unit
25 light source control unit
26 clock unit
27 large-capacity memory unit
271 patient DB
272 aggregation DB
273 polyp DB
274 polyp extraction model
74a region candidate extraction unit
74b classification unit
275 part identification model
28 light source
29 reading unit
2a portable memory medium
2b semiconductor memory
2P control program
3 display device
10a anal canal
10b rectum
10c sigmoid colon
10d descending colon
10e transverse colon
10f ascending colon
10g cecum
20a image acquisition unit
20b polyp extraction unit
20c part identification unit
20d aggregation unit
20e output unit
20f polyp classification unit
20g resection recording unit
20h operation recording unit

The invention claimed is:

1. An endoscope processor, comprising:
a processor; and
a memory including at least one set of instructions, which when executed by the processor, causes the processor to operate as:
an image acquisition processor that acquires a captured image from a large-intestine endoscope;
a part identification processor that identifies a part in a large intestine based on the captured image acquired by the image acquisition processor;
a polyp extraction processor that extracts a polyp from the captured image;
an aggregation processor that determines and aggregates a division part where the polyp exists based on a time required for the large-intestine endoscope to pass through the part where the polyp exists and a time when the polyp is captured, wherein the aggregation processor aggregates the number of polyps for each division part obtained by dividing the part identified by the part identification processor; and
an output processor that outputs an endoscope image based on the captured image and an aggregation result aggregated by the aggregation processor.

2. The endoscope processor according to claim 1, wherein the part identification processor identifies whether the part is a cecum, an ascending colon, a transverse colon, a descending colon, a sigmoid colon, or a rectum.

3. The endoscope processor according to claim 1, wherein:
the least one set of instructions, when executed by the processor, further causes the processor to operate as a polyp classification processor that classifies the polyp, as one of into a pedunculated type of polyp, a semipedunculated type of polyp, or a sessile type of polyp.

4. The endoscope processor according to claim 1, wherein:
the least one set of instructions, when executed by the processor, further causes the processor to operate as a resection recording processor that records whether the polyp has been resected,
the aggregation processor aggregates a resected polyp and an unresected polyp which are recorded in the resection recording processor, respectively.

5. The endoscope processor according to claim 1, wherein:
the least one set of instructions, when executed by the processor, further causes the processor to operate as an operation recording processor that records an operation including dye spraying performed during endoscopic examination and an operation time in association with each other, the output processor outputs an operation recorded in the operation recording processor in association with the aggregation result.

6. The endoscope processor according to claim 1, wherein the output processor outputs an endoscope image based on the captured image and a graph illustrating a relationship between a part in the large intestine and the number of polyps aggregated by the aggregation processor on one screen.

7. The endoscope processor according to claim 6, wherein the graph illustrates a relationship between a part in the large intestine and the number of the polyps and a cumulative number of the polyps.

8. The endoscope processor according to claim 1, wherein the output processor displays a tag indicating the polyp to be superimposed with the endoscope image.

9. An information processing device, comprising:
a processor; and
a memory including at least one set of instructions, which when executed by the processor, causes the processor to operate as:
  an image acquisition processor that acquires a captured image captured by a large-intestine endoscope;
  a part identification processor that identifies a part in a large intestine based on the captured image acquired by the image acquisition processor;
  a polyp extraction processor that extracts a polyp from the captured image;
    an aggregation processor that determines and aggregates a division part where the polyp exists based on a time required for the large-intestine endoscope to pass through the part where the polyp exists and a time when the polyp is captured, wherein the aggregation processor aggregates the number of polyps for each division part obtained by dividing the part identified by the part identification processor; and
  an output unit that outputs an endoscope image based on the captured image and an aggregation result aggregated by the aggregation unit processor.

10. An endoscope system, comprising:
an endoscope processor; and
a large-intestine endoscope that is connected to the endoscope processor, wherein the endoscope processor includes a memory including at least one set of instructions, which when executed by the endoscope processor, causes the endoscope processor to operate as:
  an image acquisition processor that acquires a captured image from the large- intestine endoscope,
  a part identification processor that identifies a part in a large intestine based on the captured image acquired by the image acquisition unit,
  a polyp extraction processor that extracts a polyp from the captured image,
  an aggregation processor that determines and aggregates a division part where the polyp exists based on a time required for the large-intestine endoscope to pass through the part where the polyp exists and a time when the polyp is captured, wherein the aggregation processor aggregates the number of polyps for each division part obtained by dividing the part identified by the part identification processor, and
  an output unit that outputs an endoscope image based on the captured image and an aggregation result aggregated by the aggregation processor.

\* \* \* \* \*